United States Patent
Alterman et al.

(10) Patent No.: US 8,357,710 B2
(45) Date of Patent: Jan. 22, 2013

(54) BICYCLIC ANGIOTENSIN II AGONISTS

(75) Inventors: Mathias Alterman, Stockholm (SE); Anders Hallberg, Uppsala (SE); Murugaiah Andappan Murugaiah Subbaiah, Tamil Nadu (IN)

(73) Assignee: Vicore Pharma AB, Gothenburg (SE)

( * ) Notice: Subject to any disclaimer, the term of this patent is extended or adjusted under 35 U.S.C. 154(b) by 1129 days.

(21) Appl. No.: 11/918,241

(22) PCT Filed: Apr. 12, 2006

(86) PCT No.: PCT/GB2006/001334
§ 371 (c)(1),
(2), (4) Date: Sep. 19, 2008

(87) PCT Pub. No.: WO2006/109058
PCT Pub. Date: Oct. 19, 2006

(65) Prior Publication Data
US 2009/0069382 A1    Mar. 12, 2009

Related U.S. Application Data

(60) Provisional application No. 60/670,249, filed on Apr. 12, 2005.

(51) Int. Cl.
| A61K 31/34 | (2006.01) |
| A61K 31/381 | (2006.01) |
| A61K 31/40 | (2006.01) |
| A61K 31/4174 | (2006.01) |
| A61K 31/42 | (2006.01) |
| A61K 31/425 | (2006.01) |
| C07D 207/33 | (2006.01) |
| C07D 233/20 | (2006.01) |
| C07D 333/14 | (2006.01) |
| C07D 277/22 | (2006.01) |
| C07D 307/38 | (2006.01) |

(52) U.S. Cl. ...... 514/370; 548/205; 548/234; 548/326.5; 514/377; 514/386; 514/438; 514/471; 549/74; 549/491

(58) Field of Classification Search ............... 548/190, 548/234, 326.5, 205; 514/370, 377, 386, 514/438, 471; 549/74, 491
See application file for complete search history.

(56) References Cited

U.S. PATENT DOCUMENTS

| 5,312,820 A | 5/1994 | Ashton et al. |
| 5,424,450 A | 6/1995 | Boswell et al. |
| 5,444,067 A | 8/1995 | Kivlighn et al. |
| 5,512,681 A | 4/1996 | Boswell et al. |
| 5,545,651 A | 8/1996 | Duncia et al. |

FOREIGN PATENT DOCUMENTS

| DE | 40 23 215 A1 | 1/1992 |
| EP | 0 399 731 A1 | 11/1990 |
| EP | 0 399 732 A1 | 11/1990 |
| EP | 0 499 415 A1 | 8/1992 |
| EP | 0 855 392 A | 7/1998 |
| JP | 2003-206280 | 7/2003 |
| WO | WO 93/04045 | 3/1993 |
| WO | WO 93/04046 | 3/1993 |
| WO | WO 94/11379 A1 | 5/1994 |
| WO | WO 94/28896 | 12/1994 |
| WO | WO 99/43339 A1 | 9/1999 |
| WO | WO 02/072569 A | 9/2002 |
| WO | WO 02/080439 A1 | 10/2002 |
| WO | WO 02/096883 A1 | 12/2002 |
| WO | WO 03/064414 A1 | 8/2003 |
| WO | WO 2004/046128 A | 6/2004 |
| WO | WO 2004/046128 A1 | 6/2004 |
| WO | WO 2004/046137 A1 | 6/2004 |
| WO | WO 2004/046141 A1 | 6/2004 |
| WO | WO-2004-085420 A1 * | 7/2004 |
| WO | WO-2004/085420 * | 10/2004 |
| WO | WO 2004/085420 A | 10/2004 |
| WO | WO 2004/085420 A1 | 10/2004 |

OTHER PUBLICATIONS

International Preliminary Report on Patentability; Int'l Appln. No. PCT/GB2006/001334; Int'l Filing Date Apr. 12, 2006 (8 pgs).
Ardaillou, R.; "Angiotensin II Receptors"; *J. Am. Soc. Nephrol.*, 10: pp. 530-539 (1999).
De Gasparo, M., et al; "International Union of Pharmacology. XXIII. The Angiotensin II Receptors"; *Pharmacol Rev.*; 52, ppl. 415-472 (2000).
Pandya, T., et al; "3-D QSAR Studies of Triazolinone Based Balanced $AT_1/AT_2$ Receptor Antagonists"; *Bioorganic & Medicinal Chemistry*; 9, pp. 291-300 (2001).

* cited by examiner

*Primary Examiner* — Kamal Saeed
*Assistant Examiner* — Janet L Coppins
(74) *Attorney, Agent, or Firm* — Nixon & Vanderhye

(57) ABSTRACT

There is provided a compound of formula I,

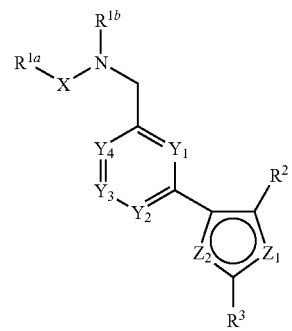

wherein $R^{1a}$, $R^{1b}$, X, $Y_1$, $Y_2$, $Y_3$, $Y_4$, $Z_1$, $Z_2$, $R^2$ and $R^3$ have meanings given in the description, and pharmaceutically-acceptable salts thereof, which compounds are useful as selective agonists of the AT2 receptor, and thus, in particular, in the treatment of inter alia gastrointestinal conditions, such as dyspepsia, IBS and MOF, and cardiovascular disorders.

19 Claims, No Drawings

BICYCLIC ANGIOTENSIN II AGONISTS

This application is the U.S. National Phase of International Application PCT/GB2006/001334, filed 12 Apr. 2006, which designated the U.S. PCT/GB2006/001334 claims priority to U.S. Provisional Application Ser. No. 60/670,249 filed 12 Apr. 2005. The entire content of these applications are incorporated herein by reference.

FIELD OF THE INVENTION

This invention relates to novel pharmaceutically-useful compounds, in particular compounds that are angiotensin II (AngII) agonists, more particularly agonists of the AngII type 2 receptor (hereinafter the AT2 receptor), and especially agonists that bind selectively to that receptor. The invention further relates to the use of such compounds as medicaments, to pharmaceutical compositions containing them, and to synthetic routes to their production.

BACKGROUND AND PRIOR ART

The endogenous hormone AngII is a linear octapeptide (Asp$^1$-Arg$^2$-Val$^3$-Tyr$^4$-Ile$^5$-His$^6$-Pro$^7$-Phe$^8$), and is the active component of the renin-angiotensin system (RAS). It is produced by the sequential processing of the pro-hormone angiotensinogen by renin and angiotensin converting enzyme (ACE).

The renin-angiotensin system (RAS) plays an important role in the regulation of blood pressure, body fluid and electrolyte homeostasis. Ang II exerts these physiological actions in many organs including the kidneys, the adrenal glands, the heart, blood vessels, the brain, the gastrointestinal tract and the reproductive organs (de Gasparo et al, *Pharmacol. Rev.* (2000) 52, 415-472).

Two main classes of AngII receptors have been identified, and designated as the type 1 receptor (hereinafter the AT1 receptor) and the AT2 receptor. The AT1 receptor is expressed in most organs, and is believed to be responsible for the majority of the biological effects of AngII. The AT2 receptor is more prevalent than the AT1 receptor in fetal tissues, the adult ovaries, the adrenal medulla and the pancreas. An equal distribution is reported in the brain and uterus (Ardaillou, *J. Am. Soc. Nephrol.*, 10, S30-39 (1999)).

Several studies in adult individuals appear to demonstrate that, in the modulation of the response following AngII stimulation, activation of the AT2 receptor has opposing effects to those mediated by the AT1 receptor.

The AT2 receptor has also been shown to be involved in apoptosis and inhibition of cell proliferation (see de Gasparo et al, supra). Further, it seems to play a role in blood pressure control. For example, it has been shown in transgenic mice lacking AT2 receptors that their blood pressure was elevated. Furthermore, it has been concluded that the AT2 receptor is involved in exploratory behaviour, pain sensitivity and thermoregulation.

The expression of AT2 receptors has also been shown to increase during pathological circumstances, such as vascular injury, wound healing and heart failure (see de Gasparo et al, supra).

The expected pharmacological effects of agonism of the AT2 receptor are described generally in de Gasparo et al, supra.

More recently, AT2 receptor agonists have been shown to be of potential utility in the treatment and/or prophylaxis of disorders of the alimentary tract, such as dyspepsia and irritable bowel syndrome, as well as multiple organ failure (see international patent application WO 99/43339).

AngII antagonists (which bind to the AT1 and/or AT2 receptors) have been disclosed in inter alia international applications WO 93/04045, WO 93/04046, WO 94/11379 and WO 94/28896, U.S. Pat. Nos. 5,312,820 and 5,512,681, European patent applications EP 0 499 415, EP 399 731 and EP 399 732 and Pandya et al, *Bioorganic & Medicinal Chemistry*, 9, 291-300 (2001). The use of the compounds disclosed in these documents as agonists of AngII, and in particular the AT2 receptor, is not contemplated.

U.S. Pat. No. 5,444,067 discloses compounds comprising an imidazolyl group attached, via a methylene bridge, to a phenylthiophene moiety, as AngII agonists. The phenyl ring of the phenylthiophene moiety in these molecules is 1,4-disubstituted with the thiophene and the imidazolyl group (which is attached via a methylene bridge).

More recently, international patent applications WO 02/96883, WO 03/064414, WO 2004/085420, WO 2004/046128, WO 2004/046141 and WO 2004/046137 have disclosed various multicyclic compounds as agonists of AngII and in particular as selective AT2 receptor agonists. In the compounds disclosed in these documents, a central aryl ring is disubstituted in the 1,4 (para) configuration. None of these documents mention or suggest compounds in which such an aryl group is disubstituted in the 1,3 (meta) configuration.

We have now found that such compounds are effective and/or selective AT2 receptor agonists and are therefore expected to find utility in inter alia the above-mentioned conditions.

DISCLOSURE OF THE INVENTION

According to the invention there is provided a compound of formula I,

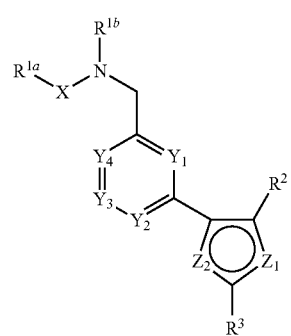

wherein
X represents —O—, —C(O)— or —S(O)$_2$—;
R$^{1a}$ and R$^{1b}$ independently represent H, C$_{1-6}$ alkyl, C$_{1-6}$ alkoxy-C$_{1-6}$ alkyl, Ar$^1$, Het$^1$, C$_{1-3}$ alkyl-Ar$^2$, C$_{1-3}$ alkyl-Het$^2$, C$_{1-3}$ alkoxy-Ar$^3$ or C$_{1-3}$ alkoxy-Het$^3$; or, in the case where X represents —C(O)—, R$^{1a}$ may also represent C$_{1-6}$ alkoxy, —O—Ar$^4$, —C(O)—C$_{1-6}$ alkoxy, —C(O)—O—Ar$^5$ or —C(O)—O-Het$^4$;
Ar$^1$, Ar$^2$, Ar$^3$, Ar$^4$ and Ar$^5$ each independently represent a C$_{6-10}$ aryl group, which group is optionally substituted by one or more substituents selected from =O, —OH, cyano, halo, nitro, C$_{1-6}$ alkyl (optionally terminated by —N(H)C(O)OR$^{11a}$), C$_{1-6}$ alkoxy, phenyl, —N(R$^{12a}$)R$^{2b}$, —C(O)R$^{12c}$, —C(O)OR$^{12d}$, —C(O)N(R$^{12e}$)R$^{12f}$, —N(R$^{12g}$)C(O)

$R^{12h}$, —$N(R^{12i})C(O)N(R^{12j})R^{12k}$, —$N(R^{12m})S(O)_2R^{11b}$, —$S(O)_nR^{11c}$, —$OS(O)_2R^{11d}$ and —$S(O)_2N(R^{12n})R^{12p}$;

$Het^1$, $Het^2$, $Het^3$ and $Het^4$ each independently represent a four- to twelve-membered heterocyclic group containing one or more heteroatoms selected from oxygen, nitrogen and/or sulfur, which heterocyclic group is optionally substituted by one or more substituents selected from =O, —OH, cyano, halo, nitro, $C_{1-6}$ alkyl (optionally terminated by —N(H)C(O)OR$^{11a}$), $C_{1-6}$ alkoxy, phenyl, —N(R$^{12a}$)R$^{12b}$, —C(O)R$^{12c}$, —C(O)OR$^{12d}$, —C(O)N(R$^{12e}$)R$^{12f}$, —N(R$^{12g}$)C(O)R$^{12h}$, N(R$^{12i}$)C(O)N(R$^{12j}$)R$^{12k}$, —N(R$^{12m}$)S(O)$_2$R$^{11b}$, —S(O)$_n$R$^{11c}$, —OS(O)$_2$R$^{11d}$ and —S(O)$_2$N(R$^{12n}$)R$^{12p}$;

$R^{11a}$ to $R^{11d}$ independently represent, on each occasion when used herein, $C_{1-6}$ alkyl;

$R^{12a}$ to $R^{12p}$ independently represent, on each occasion when used herein, H or $C_{1-6}$ alkyl;

n represents 0, 1 or 2;

$Y_1$, $Y_2$, $Y_3$ and $Y_4$ independently represent —CH— or —CF—;

$Z_1$ represents —CH—, —O—, —S—, —N— or —CH=CH—;

$Z_2$ represents —CH—, —O—, —S— or —N—;

provided that:

(a) $Z_1$ and $Z_2$ are not the same;

(b) when $Z_1$ represents —CH=CH—, then $Z_2$ may only represent —CH— or —N—; and (c) other than in the specific case in which $Z_1$ represents —CH=CH—, and $Z_2$ represents —CH—, when one of $Z_1$ and $Z_2$ represents —CH—, then the other represents —O— or —S—;

$R^2$ represents —S(O)$_2$N(H)C(O)R$^4$, —S(O)$_2$N(H)S(O)$_2$R$^4$, —C(O)N(H)S(O)$_2$R$^4$, or, when $Z_1$ represents —CH=CH—, R$^2$ may represent —N(H)S(O)$_2$N(H)C(O)R$^5$ or —N(H)C(O)N(H)S(O)$_2$R$^5$;

$R^3$ represents $C_{1-6}$ alkyl, $C_{1-6}$ alkoxy, $C_{1-6}$ alkoxy-$C_{1-6}$-alkyl or di-$C_{1-3}$-alkylamino-$C_{1-4}$-alkyl;

$R^4$ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$-alkoxy, $C_{1-6}$ alkylamino or di-$C_{1-6}$ alkylamino; and $R^5$ represents $C_{1-6}$ alkyl, or a pharmaceutically-acceptable salt thereof, which compounds and salts are referred to together hereinafter as "the compounds of the invention".

Pharmaceutically-acceptable salts include acid addition salts and base addition salts. Such salts may be formed by conventional means, for example by reaction of a free acid or a free base form of a compound of the invention with one or more equivalents of an appropriate acid or base, optionally in a solvent, or in a medium in which the salt is insoluble, followed by removal of said solvent, or said medium, using standard techniques (e.g. in vacuo or by freeze-drying). Salts may also be prepared by exchanging a counter-ion of a compound of the invention in the form of a salt with another counter-ion, for example using a suitable ion exchange resin.

Unless otherwise specified, alkyl groups, and the alkyl parts of alkoxy, alkoxyalkyl, alkoxyalkoxy, alkylamino, alkylaminoalkyl, alkyl-aryl, alkyl-heterocyclic groups, alkoxy-aryl and alkoxy-heterocyclic groups, as defined herein may be straight-chain or, when there is a sufficient number (i.e. a minimum of two or three, as appropriate) of carbon atoms, be branched-chain, and/or cyclic. Further, when there is a sufficient number (i.e. a minimum of four) of carbon atoms, such groups may also be part cyclic. Such alkyl groups, and the alkyl parts of alkoxy, alkoxyalkyl, alkoxyalkoxy, alkylamino, alkylaminoalkyl, alkyl-aryl, alkyl-heterocyclic, alkoxy-aryl and alkoxy-heterocyclic groups may also be saturated or, when there is a sufficient number (i.e. a minimum of two) of carbon atoms, be unsaturated. Unless otherwise specified, such groups may also be substituted by one or more halo, and especially fluoro, atoms.

For the avoidance of doubt, alkoxy, alkoxyalkoxy and aryloxy (e.g. —O—Ar$^4$) groups are attached to the rest of the molecule via the/an oxygen atom in that group, alkylamino groups are attached to the rest of the molecule via the nitrogen atom of the amino part of that group, alkoxyalkyl, alkylaminoalkyl, alkyl-aryl and alkyl-heterocyclic groups are attached to the rest of the molecule via the alkyl part of that group, and alkoxy-aryl and alkoxy-heterocyclic groups are attached to the rest of the molecule via the alkyl part of the alkoxy part of that group.

The term "halo", when used herein, includes fluoro, chloro, bromo and iodo.

For the avoidance of doubt, in cases in which the identity of two or more substituents in a compound of the invention (for example R$^{1a}$ and R$^{1b}$) may be the same, the actual identities of the respective substituents are not in any way interdependent. For example, in the situation in which R$^{1a}$ and R$^{1b}$ both represent $C_{1-6}$ alkyl groups, the two alkyl groups in question may be the same or different. Similarly, when aryl and heterocyclic groups are substituted by more than one substituent as defined herein, the identities of the individual substituents are not to be regarded as being interdependent.

$C_{6-10}$ aryl groups include phenyl, naphthyl and the like (preferably phenyl). Preferred optional substituents on aromatic groups include halo, —OH, cyano, nitro, $C_{1-6}$ (e.g. $C_{1-3}$) alkoxy groups and, more particularly, $C_{1-6}$ (e.g. $C_{1-3}$) alkyl groups (such as methyl).

Het (Het$^1$, Het$^2$, Het$^3$ and Het$^4$) groups that may be mentioned include those containing 1 to 4 heteroatoms (selected from the group oxygen, nitrogen and/or sulfur) and in which the total number of atoms in the ring system are between five and twelve. Het (Het$^1$, Het$^2$, Het$^3$ and Het$^4$) groups may be fully saturated, wholly aromatic, partly aromatic and/or bicyclic in character. Heterocyclic groups that may be mentioned include benzodioxanyl, benzodioxepanyl, benzodioxolyl, benzofuranyl, benzofurazanyl, benzimidazolyl, benzomorpholinyl, benzothiophenyl, chromanyl, cinnolinyl, dioxanyl, furanyl, hydantoinyl, imidazolyl, imidazo[1,2-a]pyridinyl, indolyl, isoquinolinyl, isoxazolyl, maleimido, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, 3-sulfolenyl, tetrahydropyranyl, tetrahydrofuranyl, thiazolyl, thiophenyl, thiochromanyl, triazolyl, tetrazolyl and the like. Values of Het$^1$ that may be mentioned include furanyl, pyridinyl, thiazolyl and, more particularly, thiophenyl (e.g. 2-thiophenyl). Values of Het$^2$ that may be mentioned include furanyl, thiophenyl, thiazolyl and, more particularly, pyridinyl (e.g. 3-pyridinyl). Values of Het$^3$ and Het$^4$ that may be mentioned include pyridinyl.

Substituents on Het (Het$^1$, Het$^2$, Het$^3$ and Het$^4$) groups may, where appropriate, be located on any atom in the ring system including a heteroatom. The point of attachment of Het (Het$^1$, Het$^2$, Het$^3$ and Het$^4$) groups may be via any atom in the ring system including (where appropriate) a heteroatom, or an atom on any fused carbocyclic ring that may be present as part of the ring system. Het (Het$^1$, Het$^2$, Het$^3$ and Het$^4$) groups may also be in the N- or S-oxidised form.

Preferred ring systems comprising the substituents $Y_1$, $Y_2$, $Y_3$ and $Y_4$ include phenyl groups. For the avoidance of doubt, the ring systems in compounds of formula I that comprise the groups $Z_1$ and $Z_2$, are aromatic in nature. In some instances, for example in cases where one of $Z_1$ and $Z_2$ represents —N—, the skilled person will appreciate that an additional H atom may necessarily be bonded to that N atom, in order to ensure that the rules of valency are adhered to. Preferred ring systems comprising $Z_1$ and $Z_2$ include oxazole groups, thiazole groups, pyridinyl groups, furanyl groups and, more particularly, thiophenyl groups and phenyl groups.

Compounds of the invention may exhibit tautomerism. All tautomeric forms and mixtures thereof are included within the scope of the invention.

Compounds of the invention also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric derivatives by conventional means (e.g. HPLC, chromatography over silica). All stereoisomers are included within the scope of the invention.

Preferred compounds of the invention include those in which:

X represents —C(O)— or —S(O)$_2$—;
$R^{1a}$ represents hydrogen; $C_{1-5}$ alkyl (such as methyl, butyl (e.g. n-butyl) or cyclic $C_{3-5}$ alkyl (e.g. cyclopropyl)); $Ar^1$ (e.g. phenyl); $Het^1$ (such as thiophenyl (e.g. 2-thiophenyl)); or, in the case where X represents —C(O)—, $C_{1-4}$ alkoxy (e.g. ethoxy) or —C(O)—$C_{1-3}$ alkoxy (e.g. —C(O)-ethoxy);
$R^{1b}$ represents $C_{1-4}$ (e.g. $C_{1-3}$) alkyl (such as methyl or ethyl), which alkyl group is optionally substituted by one or more fluoro atoms; $Ar^1$, such as phenyl optionally substituted (e.g. in the 4-position) by one or more (e.g. one) $C_{1-3}$ alkyl (e.g. methyl or ethyl) groups; $C_{1-2}$ alkyl-$Ar^2$, such as —CH$_2$—$Ar^2$; or $C_{1-2}$ alkyl-$Het^2$, such as —CH$_2$-$Het^2$;
$Ar^2$ represents unsubstituted phenyl;
$Het^2$ represents pyridinyl (e.g. 3-pyridinyl) group;
$Y_1, Y_2, Y_3$ and $Y_4$ all represent —CH—;
$Z_1$ represents —CH=CH— or, more preferably, —S—;
$Z_2$ represents —CH—;
$R^2$ represents —S(O)$_2$N(H)C(O)R$^4$;
$R^3$ represents $C_{1-4}$ alkyl, such as n-butyl or, particularly, iso-butyl;
$R^4$ represents $C_{1-4}$ alkyl such as n-butyl, preferably $C_{1-4}$ alkoxy-$C_{1-3}$ alkyl such as n-butoxymethyl or, more preferably, $C_{1-4}$ alkoxy such as iso-butoxy and especially, n-butoxy.

When X represents —S(O)$_2$—, preferred values of $R^{1a}$ include $Het^1$.

When $R^2$ represents —S(O)$_2$N(H)C(O)R$^4$, —S(O)$_2$N(H)S(O)$_2$R$^4$ or —C(O)N(H)S(O)$_2$R$^4$, preferred values of $R^4$ include n-butoxymethyl, iso-butoxy and especially, n-butoxy.

More preferred compounds of the invention include the compounds of the examples described hereinafter.

Compounds of formula I may be made in accordance with techniques well known to those skilled in the art, for example as described hereinafter.

According to a further aspect of the invention there is provided a process for the preparation of a compound of formula I, which process comprises:

(i) for compounds of formula I in which $R^2$ represents —S(O)$_2$N(H)C(O)R$^4$ or —S(O)$_2$N(H)S(O)$_2$R$^4$, and $R^4$ is as hereinbefore defined, reaction of a compound of formula II,

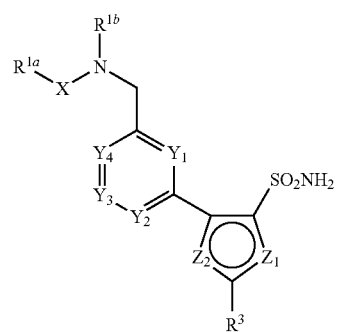

wherein $R^{1a}$, $R^{1b}$, X, $Y_1$, $Y_2$, $Y_3$, $Y_4$, $Z_1$, $Z_2$ and $R^3$ are as hereinbefore defined with a compound of formula III, $$R^4GL^1 \qquad\qquad III$$

wherein G represents —C(O)— or —S(O)$_2$— (as appropriate), $L^1$ represents a suitable leaving group, such as halo (e.g. chloro or bromo) and $R^4$ is as hereinbefore defined, for example at around room temperature or above (e.g. up to 60-70° C.) in the presence of a suitable base (e.g. pyrrolidinopyridine, pyridine, triethylamine, tributylamine, trimethylamine, dimethylaminopyridine, di-iso-propylamine, 1,8-diazabicyclo[5.4.0]undec-7-ene, sodium hydroxide, sodium carbonate, or mixtures thereof) and an appropriate solvent (e.g. pyridine, dichloromethane, chloroform, tetrahydrofuran, dimethylformamide, trifluoromethylbenzene, triethylamine, water, or mixtures thereof). Preferred base/solvent systems for compounds of formula III in which G is —C(O)— include pyrrolidinopyridine/pyridine, pyrrolidinopyridine/triethylamine, dimethylaminopyridine/pyridine, dimethylaminopyridine/triethylamine, sodium carbonate/dichloromethane/water or pyrrolidinopyridine/triethylamine/dichloromethane. Preferred base/solvent systems for compounds of formula III in which G is —S(O)$_2$— include NaOH/THF;

(ii) for compounds of formula I in which $R^2$ represents —S(O)$_2$N(H)C(O)R$^4$ and $R^4$ represents $C_{1-6}$ alkoxy-$C_{1-6}$-alkyl, coupling of a compound of formula II as hereinbefore defined with a compound of formula IV, $$R^{4a}CO_2H \qquad\qquad IV$$

wherein $R^{4a}$ represents $C_{1-6}$ alkoxy-$C_{1-6}$-alkyl, for example under similar conditions to those described under process step (i) above, in the presence of a suitable coupling reagent (e.g. 1,1'-carbonyl-diimidazole, N,N'-dicyclohexylcarbodiimide, N,N'-disuccinimidyl carbonate, benzotriazole-1-yloxytris(dimethylamino)phosphoniumhexafluorophosphate, 2-(1H-benzotriazole-1-yl)-1,1,3,3-tetramethyluronium hexafluorophosphate, benzotriazole-1-yl-oxy-tris-pyrrolidino-phosphonium hexafluorophosphate, bromo-tris-pyrrolidinophosphonium hexafluorophosphate or 2-(1H-benzotriazole-1-yl)-1,1,3,3-tetramethyluronium tetrafluorocarbonate), a suitable base (as mentioned in process step (i) above) and an appropriate solvent (as mentioned in process step (i) above);

(iii) for compounds of formula I in which $R^2$ represents —C(O)N(H)S(O)$_2$R$^4$ and $R^4$ is as hereinbefore defined, coupling of a compound of formula V,

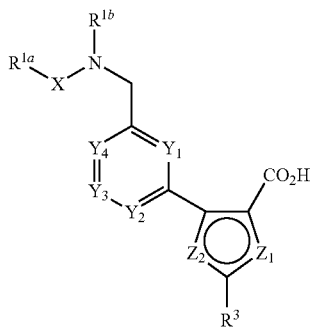

V wherein $R^{1a}$, $R^{1b}$, X, $Y_1$, $Y_2$, $Y_3$, $Y_4$, $Z_1$, $Z_2$ and $R^3$ are as hereinbefore defined with a compound of formula VI,

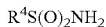 VI wherein $R^4$ is as hereinbefore defined, for example in the presence of a suitable coupling reagent (such as those described in process step (ii) hereinbefore), and under similar reaction conditions to those described hereinbefore for preparation of compounds of formula I in which $R^2$ represents —S(O)$_2$N(H)C(O)R$^4$ and $R^4$ represents $C_{1-6}$ alkoxy-$C_{1-6}$-alkyl (i.e. process step (ii));

(iv) for compounds of formula I in which $R^2$ represents —C(O)N(H)S(O)$_2$R$^4$ and $R^4$ is as hereinbefore defined, coupling of a compound of formula VII,

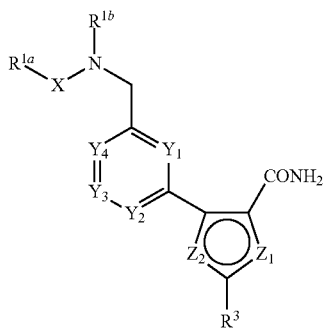

VII wherein $R^{1a}$, $R^{1b}$, X, $Y_1$, $Y_2$, $Y_3$, $Y_4$, $Z_1$, $Z_2$ and $R^3$ are as hereinbefore defined with a compound of formula VIII,

 VIII wherein $R^4$ is as hereinbefore defined, for example at around 50° C. in the presence of a suitable base (e.g. sodium hydride) and an appropriate organic solvent (e.g. THF);

(v) for compounds of formula I in which $R^2$ represents —N(H)S(O)$_2$N(H)C(O)R$^5$ and $R^5$ is as hereinbefore defined, reaction of a compound of formula IX,

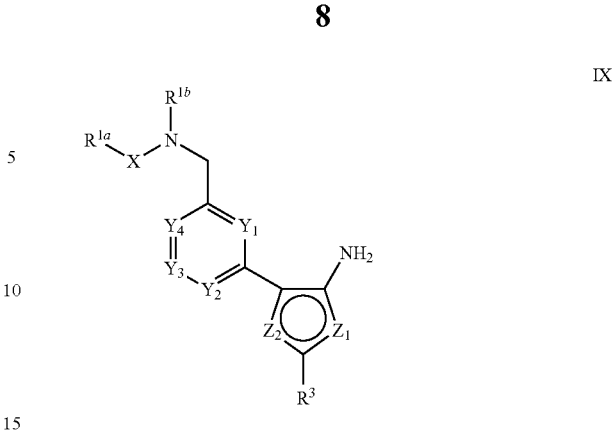

IX wherein $R^{1a}$, $R^{1b}$, X, $Y_1$, $Y_2$, $Y_3$, $Y_4$, $Z_1$, $Z_2$ and $R^3$ are as hereinbefore defined with a compound of formula X,

 X wherein $R^5$ is as hereinbefore defined, for example at or around room temperature in the presence of a suitable base (e.g. sodium hydroxide or triethylamine) and a suitable organic solvent (e.g. benzene or dichloromethane);

(vi) for compounds of formula I in which $R^2$ represents —N(H)C(O)N(H)S(O)$_2$R$^5$ and $R^5$ is as hereinbefore defined, reaction of a compound of formula IX as hereinbefore defined with a compound of formula XI,

 XI wherein $R^x$ represents a suitable leaving group, such as a halo (e.g. chloro or bromo) group or alkoxy (e.g. —O—$C_{1-2}$ alkyl) and $R^5$ is as hereinbefore defined, for example at or around room temperature in the presence of a suitable organic solvent (e.g. dichloromethane). Alternatively Rx may represent —OH, in which case the coupling reaction may be performed under conditions such as those hereinbefore described in respect of process (ii) above;

(vii) for compounds of formula I in which $R^2$ represents —N(H)C(O)N(H)S(O)$_2$R$^5$ and $R^5$ is as hereinbefore defined, reaction of a compound of formula IX as hereinbefore defined with an isocyanate compound of formula XII,

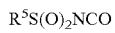 XII wherein $R^5$ is as hereinbefore defined, for example at or around room temperature in the presence of a suitable organic solvent (e.g. dichloromethane);

(viii) for compounds of formula I in which $R^2$ represents —S(O)$_2$N(H)C(O)R$^4$ and $R^4$ represents $C_{1-6}$ alkylamino, reaction of a compound of formula II as hereinbefore defined with an isocyanate compound of formula XIII,

 XIII wherein $R^{4b}$ is $C_{1-6}$ alkyl, for example at or around room temperature in the presence of a suitable base (e.g. sodium hydroxide or potassium hydroxide and an appropriate organic solvent (e.g. acetone or acetonitrile);

(ix) for compounds of formula I in which $R^2$ represents —S(O)$_2$N(H)C(O)R$^4$ and $R^4$ represents di-$C_{1-6}$ alkylamino, reaction of a corresponding compound of formula I in which $R^2$ represents —S(O)$_2$N(H)C(O)R$^4$ and $R^4$ represents $C_{1-6}$ alkoxy with an amine of formula XIIIa,

 XIIIa wherein $R^{4c}$ and $R^{4d}$ independently represent $C_{1-6}$ alkyl, for example at above room temperature (e.g. at between 70° C. and 100° C.) in the presence of an appropriate organic solvent (e.g. toluene); or (x) for compounds of formula I in which X represents —O—, reductive amination of a compound of formula XIV,

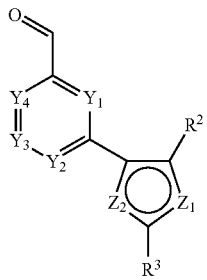

XIV wherein $Y_1$, $Y_2$, $Y_3$, $Y_4$, $Z_1$, $Z_2$, $R^2$ and $R^3$ are as hereinbefore defined, in the presence of a compound of formula XV,

 XV wherein $R^{1a}$ and $R^{1b}$ are as hereinbefore defined under standard conditions (e.g. in the presence of a suitable organic solvent (e.g. methanol, ethanol, dichloromethane, dichloroethane, tetrahydrofuran or dioxane), and, subsequently, an appropriate reducing agent (e.g. sodium borohydride, sodium cyanoborohydride or $NaBH(OAc)_3$)). The skilled person will appreciate that this reductive amination may be performed in one pot (as well as sequentially), using a chemoselective reducing agent, such as the latter two reducing agents described above.

Compounds of formula V may be prepared by oxidation of a compound of formula XVI,

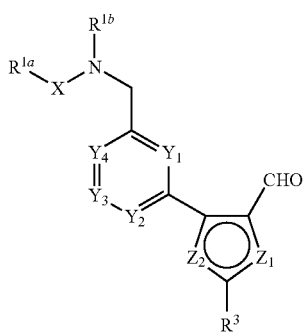

XVI wherein $R^{1a}$, $R^{1b}$, X, $Y_1$, $Y_2$, $Y_3$, $Y_4$, $Z_1$, $Z_2$ and $R^3$ are as hereinbefore defined, for example under standard oxidation conditions in the presence of a suitable oxidising agent, such as potassium permanganate or chromium (VI) oxide.

Compounds of formulae II, VII, IX and XVI in which X represents —C(O)— or —S(O)$_2$— may be prepared by reaction of a compound of formula XVII,

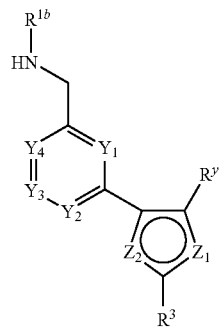

XVII wherein $R^y$ represents —SO$_2$NH$_2$ (in the case of a compound of formula II), —CONH$_2$ (in the case of a compound of formula VII), —NH$_2$ (in the case of a compound of formula IX), or —CHO (in the case of a compound of formula XVI), and $R^{1b}$, $Y_1$, $Y_2$, $Y_3$, $Y_4$, $Z_1$, $Z_2$ and $R^3$ are as hereinbefore defined, with a compound of formula XVIII,

 XVIII wherein $X^a$ represents —C(O)— or —S(O)$_2$— and $R^{1a}$ and $L^1$ are as hereinbefore defined, for example at or around room temperature in the presence of a suitable base (e.g. triethylamine, 4-dimethylaminopyridine, pyrrolidinopyridine, diisopropylethylamine or mixtures thereof) and an appropriate organic solvent (e.g. dichloromethane, chloroform, tetrahydrofuran, dioxane or dimethylformamide). Alternatively, compounds of formulae II, VII, IX and XVI in which $R^{1a}$ represents H and X represents —C(O)— may be prepared in this way by reaction of a compound of formula XVII with ammonium formate, for example at above room temperature (e.g. between 80 to 120° C.) in the presence of an appropriate organic solvent (e.g. acetonitrile, dioxane, dimethylformamide, ethylene glycol dimethyl ether, 1-methyl-2-pyrrolidinone or dimethylsulphoxide). Preferably compounds of formula XVII are protected at the $R^y$ position prior to carrying out the reaction with the compound of formula XVIII or ammonium formate. Suitable protecting groups for different values of $R^y$ are described hereinafter. If a protected version of a compound of formula XVII is employed, this reaction may be followed by deprotection of the $R^y$ group under standard conditions, for example as described hereinafter.

Compounds of formulae II, VII, IX or XVI in which X represents —C(O)— or —S(O)$_2$— may alternatively be prepared by reaction of a compound of formula XIX,

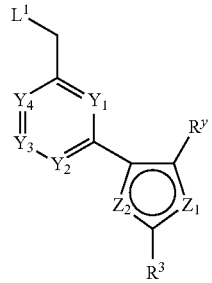

XIX wherein $L^1$, $Y_1$, $Y_2$, $Y_3$, $Y_4$, $Z_1$, $Z_2$, $R^3$ and $R^y$ are as hereinbefore defined ($L^1$ may, in particular, represent bromo), with a compound of formula XX,

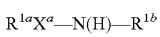 XX wherein $R^{1a}$, $X^a$ and $R^{1b}$ are as hereinbefore defined, for example at around or below room temperature in the presence of a suitable base (e.g. potassium hydroxide, potassium tert-butoxide, triethylamine or di-iso-propylethylamine) and an appropriate organic solvent (e.g. DMSO, DMF, THF or $CH_2Cl_2$). As with compounds of formula XVII, compounds of formula XIX are preferably protected at the $R^y$ position prior to carrying out the reaction with the compound of formula XX. If a protected version of a compound of formula XIX is employed, this reaction may be followed by deprotection of the $R^y$ group under standard conditions, for example as described hereinafter.

Compounds of formulae II, VII, IX and XVI may alternatively be prepared by reaction of a compound of formula XXI,

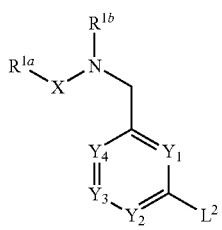

XXI wherein $L^2$ represents a suitable leaving group, such as methylsulphonate (e.g. trifluoromethylsulphonate), or halo, such as iodo or bromo, and $R^{1a}$, $R^{1b}$, X, $Y_1$, $Y_2$, $Y_3$ and $Y_4$ are as hereinbefore defined, with a compound of formula XXII,

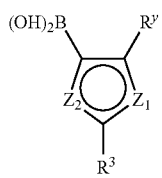

XXII wherein $R^y$, $R^3$, $Z^1$ and $Z^2$ are as hereinbefore defined, or a protected derivative thereof, for example in the presence of an appropriate coupling catalyst system (e.g. a palladium catalyst, such as $Pd(PPh_3)_4$ or $Pd(OAc)_2$/ligand (wherein the ligand may be, for example, $PPh_3$, $P(o\text{-}Tol)_3$ or 1,1'-bis(diphenylphosphino)ferrocene)) and a suitable base (e.g. sodium hydroxide, sodium carbonate, potassium carbonate, cesium carbonate, cesium fluoride, triethylamine or di-iso-propylamine)), as well as a suitable solvent system (e.g. toluene, ethanol, dimethoxymethane, dimethylformamide, ethylene glycol dimethyl ether, water, dioxane or mixtures thereof). This reaction may be carried out at above room temperature (e.g. at the reflux temperature of the solvent system that is employed).

Compounds of formulae II, VII, IX and XVI in which X represents —O— may alternatively be prepared by reaction of a compound of formula XXIII,

XXIII

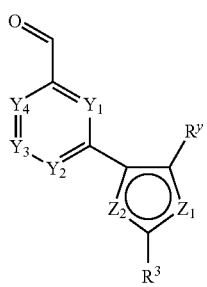

wherein $Y_1$, $Y_2$, $Y_3$, $Y_4$, $Z_1$, $Z_2$, $R^3$ and $R^y$ are as hereinbefore defined, or an appropriate protected derivative thereof, with a compound of formula XV as hereinbefore defined, for example under conditions such as those described hereinbefore for preparation of compounds of formula I.

Compounds of formula XIV may be prepared by reaction of a compound of formula XXIV,

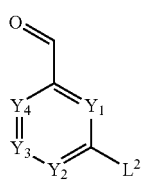

XXIV wherein $L^2$, $Y_1$, $Y_2$, $Y_3$ and $Y_4$ are as hereinbefore defined with a compound of formula XXV,

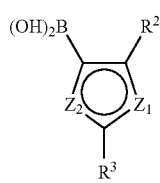

XXV wherein $R^2$, $R^3$, $Z_1$ and $Z_2$ are as hereinbefore defined, for example under similar conditions to those described hereinbefore for preparation of compounds of formulae II, VII, IX and XVI (third process).

Compounds of formula XV are readily available. For example compounds of formula XV may be prepared by reaction of a compound of formula XXVI, $R^{1b}NH_2$     XXVI wherein $R^{1b}$ is as hereinbefore defined, with an appropriate oxidising agent (for example hydrogen peroxide or meta-chloroperbenzoic acid), for example in the presence of a suitable solvent (such as ethanol or methanol), followed by reaction of the intermediate hydroxylamine ($R^{1b}N(H)OH$) with a compound of formula XXVII, $R^{1a}L^1$     XXVII wherein $L^1$ and $R^{1a}$ are as hereinbefore defined, for example in the presence of a suitable base (e.g. sodium hydride, sodium bicarbonate, sodium hydroxide or triethylamine) and an appropriate organic solvent (e.g. dioxane, dichloromethane, dimethylformamide and/or acetone). Compounds of formula XV may alternatively be prepared by reaction of an alcohol of formula XXVIII, $R^{1a}OH$     XXVIII wherein $R^{1a}$ is as hereinbefore defined, with chloramine ($NH_2Cl$), for example in the presence of an appropriate base (e.g. sodium hydride, sodium hydroxide or triethylamine) and a suitable solvent (such as diethyl ether, dioxane, dimethylformamide or dichloromethane), followed by reaction of the intermediate oxylamine ($R^{1a}ONH_2$) with a compound of formula XXIX, $R^{1b}L^1$     XXIX wherein $L^1$ and $R^{1b}$ are as hereinbefore defined, for example in the presence of a suitable base (e.g. sodium hydride, sodium bicarbonate, sodium hydroxide or triethylamine) and an appropriate organic solvent (e.g. dioxane, dichloromethane, dimethylformamide and/or acetone).

Compounds of formula XVII may be prepared by reductive amination of a compound of formula XXIII as hereinbefore defined, or an appropriate protected derivative thereof, in the presence of an amine of formula XXVI as hereinbefore defined, for example under standard conditions, such as those described hereinbefore for preparation of compounds of formula I.

Compounds of formula XIX may be prepared by conversion of the —OH group in a compound of formula XXX,

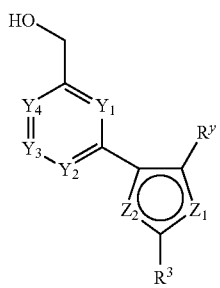

XXX wherein $Y_1$, $Y_2$, $Y_3$, $Y_4$, $Z_1$, $Z_2$, $R^3$ and $R^y$ are as hereinbefore defined, or an appropriate protected derivative thereof, to an appropriate leaving group, $L^1$ (e.g., in the case where $L^1$ is bromo, conversion may be carried out by reaction with $CBr_4$, for example at or around room temperature in the presence of a base (e.g. triphenylphosphine) and a suitable organic solvent (e.g. DMF)). Alternatively, the hydroxyl group may be converted to a sulfonate leaving group (e.g. mesylate or triflate) by employing a suitable reagent (e.g. a sulfonyl halide such as tosyl chloride, mesyl chloride or triflic anhydride).

Compounds of formula XXI may be prepared from compounds of formula XXXI,

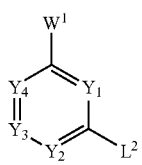

XXXI wherein $W^1$ represents —CHO, —CH$_2$OH or —CH$_2$NH$_2$ and $L^2$, $Y_1$, $Y_2$, $Y_3$ and $Y_4$ are as hereinbefore defined by way of standard techniques, for example by way of known techniques for the conversion of a —CHO, a —CH$_2$OH or a —CH$_2$NH$_2$ group into a

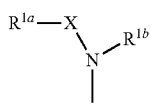

group (and in the case of —CHO and —CH$_2$OH groups analogously to methods described hereinbefore).

Compounds of formula XXII and protected derivatives thereof may be prepared by reaction of a corresponding compound of formula XXXII,

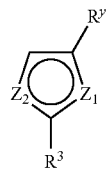

XXXII wherein $R^y$, $R^3$, $Z_1$ and $Z_2$ are as hereinbefore defined, or an appropriate protected derivative thereof, with a reagent system that will enable the introduction of —B(OH)$_2$ into the appropriate ring system. Suitable reagent systems include trialkylborates (e.g. tri-iso-propylborate). Such reactions may be carried out, for example, at low temperature (e.g. between –100° C. and 0° C., e.g. between –80° C. (such as –78° C.) and –10° C. (such as –20° C.)) in the presence of a suitable base (e.g. n-butyl lithium) and an appropriate organic solvent (e.g. THF), followed by acid hydrolysis (e.g. in the presence of dilute HCl).

Compounds of formula XXV may be prepared from corresponding compounds of formula XXII as hereinbefore defined, for example using analogous methods to those described hereinbefore for conversion of the various $R^y$ groups to the relevant $R^2$ groups (see, for example, processes for the preparation of compounds of formula I).

Compounds of formulae XXIII and XXX may be prepared by reaction of a compound of formula XXXI as hereinbefore defined (in which former case, $W^1$ represents —CHO and in which latter case, $W^1$ represents —CH$_2$OH), with a compound of formula XXII as hereinbefore defined, or an appropriate protected derivative thereof, for example under similar conditions to those described hereinbefore for preparation of compounds of formulae II, VII, IX and XVI (third process).

Compounds of formula XXXII are available using known techniques. For example:

(a) Compounds of formula XXXII in which $R^y$ represents —S(O)$_2$NH$_2$, —C(O)NH$_2$ or —CHO, and protected derivatives thereof, may be prepared by reaction of a compound of formula XXXIII,

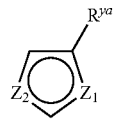

XXXIII wherein $R^{ya}$ represents —S(O)$_2$NH$_2$, —C(O)NH$_2$ or —CHO and $Z_1$ and $Z_2$ are as hereinbefore defined, or a protected derivative thereof, with a compound of formula XXXIV, $R^3L^3$  XXXIV wherein $L^3$ represents a suitable leaving group (such as toluenesulphonate, benzenesulphonate, methanesulphonate or halo, such as bromo or iodo) and $R^3$ is as hereinbefore defined, for example at below room temperature (e.g. between around –35° C. and around –85° C.), in the presence of a suitable base (e.g. n-butyl lithium) and an appropriate solvent (e.g. THF).

(b) Compounds of formula XXXII in which $R^y$ is —S(O)$_2$NH$_2$ and N-protected derivatives thereof, may be prepared by reaction of an appropriate compound of formula XXXV,

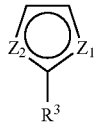

XXXV wherein $R^3$, $Z_1$ and $Z_2$ are as hereinbefore defined with an appropriate reagent for introduction of a —S(O)$_2$NH$_2$ group into the appropriate ring system (for example chlorosulphonic acid, or thionyl chloride in the presence of a suitable strong base (e.g. butyl lithium)), followed by reaction of the resultant intermediate with ammonia, or a protected derivative thereof (e.g. tert-butylamine), under conditions that are well known to those skilled in the art.

(c) Certain protected derivatives (e.g. alkyl, such as C$_{1-6}$ alkyl, for example tert-butyl, protected derivatives) of compounds of formula XXXII in which $R^y$ represents —C(O)NH$_2$ may be prepared by reaction of a compound of formula XXXV as hereinbefore defined, with a compound of formula XXXVI,

R$^Z$N=C=O  XXXVI wherein R$^Z$ represents an appropriate protecting group, such as an alkyl group, including C$_{1-6}$ alkyl, e.g. tert-butyl for example at around 0° C., in the presence of a suitable base (e.g. n-butyl lithium) and an appropriate solvent (e.g. THF).

(d) Certain protected derivatives (e.g. alkyl, such as C$_{1-6}$ alkyl, for example tert-butyl, protected derivatives) of compounds of formula XXXII in which $R^y$ represents —C(O)NH$_2$ may also be prepared by reaction of a compound of formula XXXVII,

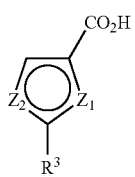

XXXVII wherein $R^3$, $Z_1$ and $Z_2$ are as hereinbefore defined with a protected (e.g. an (e.g. C$_{1-6}$) alkyl, such as tert-butyl-protected) derivative of ammonia (e.g. tert-butylamine) under standard coupling conditions (see, for example, those described hereinbefore for preparation of compounds of formula I (process step (iii))). Compounds of formula XXXVII are known in the art or may be prepared by way of standard techniques, for example oxidation of a corresponding compound of formula XXXII in which $R^y$ is —CHO e.g. under those conditions described hereinbefore for preparation of compounds of formula V.

(e) Compounds of formula XXXII in which $R^y$ is —CHO, $Z_1$ represents —CH=CH— and $Z_2$ represents —CH—, and protected derivatives thereof, may be prepared by reaction of a compound of formula XXXV in which $Z_1$ represents —CH=CH— and $Z_2$ represents —CH— with an appropriate reagent system for the introduction of an aldehyde group into the benzene ring (e.g. Zn(CN)$_2$ and HCl or, preferably, TiCl$_4$/CHCl$_3$, SnCl$_4$/CH$_2$Cl$_2$ or 1,3,5,7-azaadamantane/TFA) under standard reaction conditions, followed by (if appropriate) protection of the resultant benzaldehyde under standard conditions.

(f) Compounds of formula XXXII in which $R^y$ is —NH$_2$, $Z_1$ represents —CH=CH— and $Z_2$ represents —CH—, and N-protected derivatives thereof, may be prepared by nitration of a compound of formula XXXV in which $Z_1$ represents —CH=CH— and $Z_2$ represents —CH—, followed by reduction of the resultant nitrobenzene and (if appropriate) protection of the resultant aminobenzene, all of which steps may be carried out under standard conditions.

Compounds of formulae III, IV, VI, VIII, X, XI, XII, XIII, XIIIa, XVIII, XX, XXIV, XXVI, XXVII, XXVIII, XXIX, XXXI, XXXIII, XXXIV, XXXV, XXXVI and XXXVII are either commercially available, are known in the literature, or may be obtained either by analogy with the processes described herein, or by conventional synthetic procedures, in accordance with standard techniques, from readily available starting materials using appropriate reagents and reaction conditions.

Compounds of the invention may be isolated from their reaction mixtures using conventional techniques.

It will be appreciated by those skilled in the art that, in the processes described above and hereinafter, the functional groups of intermediate compounds may need to be protected by protecting groups.

Functional groups that it is desirable to protect include sulphonamido, amido, amino and aldehyde. Suitable protecting groups for sulphonamido, amido and amino include tert-butyloxycarbonyl, benzyloxycarbonyl, 2-trimethylsilylethoxycarbonyl (Teoc) or tert-butyl. Suitable protecting groups for aldehyde include alcohols, such as methanol or ethanol, and diols, such as 1,3-propanediol or, preferably, 1,2-ethanediol (so forming a cyclic acetal).

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques (e.g. using a protic acid or a Lewis acid such as trifluoroacetic acid, sulfuric acid, toluenesulfonic acid, boron trichloride or Sc(OTf)$_3$).

Persons skilled in the art will appreciate that, in order to obtain compounds of the invention in an alternative, and, on some occasions, more convenient, manner, the individual process steps mentioned hereinbefore may be performed in a different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The type of chemistry involved will dictate the need, and type, of protecting groups as well as the sequence for accomplishing the synthesis.

The use of protecting groups is fully described in "*Protective Groups in Organic Chemistry*", edited by J W F McOmie, Plenum Press (1973), and "*Protective Groups in Organic Synthesis*", 3$^{rd}$ edition, T. W. Greene & P. G. M. Wutz, Wiley-Interscience (1999).

Medical and Pharmaceutical Uses

Compounds of the invention are useful because they possess pharmacological activity. The compounds of the invention are therefore indicated as pharmaceuticals.

According to a further aspect of the invention there is thus provided the compounds of the invention for use as pharmaceuticals.

In particular, compounds of the invention are agonists of AngII, more particularly, are agonists of the AT2 receptor, and, especially, are selective agonists of that sub-receptor, for example as may be demonstrated in the tests described below.

The compounds of the invention are thus expected to be useful in those conditions in which endogenous production of AngII is deficient and/or where an increase in the effect of AngII is desired or required.

The compounds of the invention are further expected to be useful in those conditions where AT2 receptors are expressed and their stimulation is desired or required.

The compounds of the invention are further indicated in the treatment of conditions characterised by vasoconstriction, increased cell growth and/or differentiation, increased cardiac contractility, increased cardiovascular hypertrophy, and/or increased fluid and electrolyte retention.

The compounds of the invention are further indicated in the treatment of stress-related disorders, and/or in the improvement of microcirculation and/or mucosa-protective mechanisms.

Thus, compounds of the invention are expected to be useful in the treatment of disorders, which may be characterised as indicated above, and which are of, for example, the gastrointestinal tract, the cardiovascular system, the respiratory tract, the kidneys, the eyes, the female reproductive (ovulation) system and the central nervous system (CNS).

Disorders of the gastrointestinal tract that may be mentioned include oesophagitis, Barrett's oesophagus, gastric ulcers, duodenal ulcers, dyspepsia (including non-ulcer dyspepsia), gastro-oesophageal reflux, irritable bowel syndrome (IBS), inflammatory bowel disease (IBD), pancreatitis, hepatic disorders (such as hepatitis), gall bladder disease, multiple organ failure (MOF) and sepsis. Other gastrointestinal disorders that may be mentioned include xerostomia, gastritis, gastroparesis, hyperacidity, disorders of the biliary tract, coelicia, Crohn's disease, ulcerative colitis, diarrhea, constipation, colic, dysphagia, vomiting, nausea, indigestion and Sjögren's syndrome.

Disorders of the respiratory tract that may be mentioned include inflammatory disorders, such as asthma, obstructive lung diseases (such as chronic obstructive lung disease), pneumonitis, pulmonary hypertension and adult respiratory distress syndrome.

Disorders of the kidneys that may be mentioned include renal failure, nephritis and renal hypertension.

Disorders of the eyes that may be mentioned include diabetic retinopathy, premature retinopathy and retinal microvascularisation.

Disorders of the female reproductive system that may be mentioned include ovulatory dysfunction.

Cardiovascular disorders that may be mentioned include hypertension, cardiac hypertrophy, cardiac failure, artherosclerosis, arterial thrombosis, venous thrombosis, endothelial dysfunction, endothelial lesions, post-balloon dilatation stenosis, angiogenesis, diabetic complications, microvascular dysfunction, angina, cardiac arrhythmias, claudicatio intermittens, preeclampsia, myocardial infarction, reinfarction, ischaemic lesions, erectile dysfunction and neointima proliferation.

Disorders of the CNS that may be mentioned include cognitive dysfunctions, dysfunctions of food intake (hunger/satiety) and thirst, stroke, cerebral bleeding, cerebral embolus and cerebral infarction.

Compounds of the invention may also be useful in the modulation of growth metabolism and proliferation, for example in the treatment of hypertrophic disorders, prostate hyperplasia, autoimmune disorders, psoriasis, obesity, neuronal regeneration, the healing of ulcers, inhibition of adipose tissue hyperplasia, stem cell differentiation and proliferation, cancer (e.g. in the gastrointestinal tract, lung cancer, etc), apoptosis, tumours (generally) and hypertrophy, diabetes, neuronal lesions and organ rejection.

The compounds of the invention are indicated both in the therapeutic and/or prophylactic treatment of the above conditions.

According to a further aspect of the present invention, there is provided a method of treatment of a condition in which endogenous production of AngII is deficient, and/or a condition where an increase in the effect of AngII is desired or required, and/or a condition where AT2 receptors are expressed and their stimulation is desired or required, which method comprises administration of a therapeutically effective amount of a compound of the invention to a person suffering from, or susceptible to, such a condition.

The compounds of the invention will normally be administered orally, intravenously, subcutaneously, buccally, rectally, dermally, nasally, tracheally, bronchially, by any other parenteral route or via inhalation, in a pharmaceutically acceptable dosage form.

When the condition to be treated is multiple organ failure, preferred routes of administration are parenteral (e.g. by injection). Otherwise, the preferred route of administration for compounds of the invention is oral.

The compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like.

Such formulations may be prepared in accordance with standard and/or accepted pharmaceutical practice.

According to a further aspect of the invention there is thus provided a pharmaceutical formulation including a compound of the invention, in admixture with a pharmaceutically acceptable adjuvant, diluent or carrier.

Compounds of the invention may also be administered in combination with other AT2 agonists that are known in the art, as well as in combination with AT1 receptor antagonists that are known in the art, such as losartan, or in combination with an inhibitor of angiotensin converting enzyme (ACE).

According to a further aspect of the invention, there is provided a combination product comprising:
(A) a compound of the invention; and
(B) an AT1 receptor antagonist, or an ACE inhibitor,
wherein each of components (A) and (B) is formulated in admixture with a pharmaceutically-acceptable adjuvant, diluent or carrier.

Such combination products provide for the administration of compound of the invention in conjunction with an AT1 receptor antagonist, or an ACE inhibitor, and may thus be presented either as separate formulations, wherein at least one of those formulations comprises compound of the invention, and at least one comprises AT1 receptor antagonist, or ACE inhibitor, or may be presented (i.e. formulated) as a combined preparation (i.e. presented as a single formulation including compound of the invention and AT1 receptor antagonist or ACE inhibitor).

Thus, there is further provided:
(1) a pharmaceutical formulation including a compound of the invention and an AT1 receptor antagonist, or an ACE inhibitor, in admixture with a pharmaceutically-acceptable adjuvant, diluent or carrier; and
(2) a kit of parts comprising components:
(a) a pharmaceutical formulation including a compound of the invention, in admixture with a pharmaceutically-acceptable adjuvant, diluent or carrier; and
(b) a pharmaceutical formulation including an AT1 receptor antagonist, or an ACE inhibitor, in admixture with a pharmaceutically-acceptable adjuvant, diluent or carrier,
which components (a) and (b) are each provided in a form that is suitable for administration in conjunction with the other.

Depending upon the disorder and patient to be treated and the route of administration, the compounds of the invention may be administered at varying doses.

Although doses will vary from patient to patient, suitable daily doses are in the range of about 1 to 1000 mg per patient, administered in single or multiple doses. More preferred daily doses are in the range 2.5 to 250 mg per patient.

Individual doses of compounds of the invention may be in the range 1 to 100 mg.

In any event, the physician, or the skilled person, will be able to determine the actual dosage which will be most suitable for an individual patient, which is likely to vary with the condition that is to be treated, as well as the age, weight, sex and response of the particular patient to be treated. The above-mentioned dosages are exemplary of the average case; there can, of course, be individual instances where higher or lower dosage ranges are merited, and such are within the scope of this invention.

Compounds of the invention have the advantage that they bind selectively to, and exhibit agonist activity at, the AT2 receptor. By compounds which "bind selectively" to the AT2 receptor, we include that the affinity ratio for the relevant compound (AT2:AT1) is at least 5:1, preferably at least 10:1 and more preferably at least 20:1.

The compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art.

Biological Tests

The following test procedures may be employed.

Test A

Receptor Binding Assay Using Rat Liver Membrane $AT_1$ Receptor

Rat liver membranes were prepared according to the method of Dudley et al (*Mol. Pharmacol.* (1990) 38, 370). Binding of [$^{125}$I]Ang II to membranes was conducted in a final volume of 0.5 mL containing 50 mM Tris-HCl (pH 7.4), 100 mM NaCl, 10 mM $MgCl_2$, 1 mM EDTA, 0.025% bacitracin, 0.2% BSA (bovine serum albumin), liver homogenate corresponding to 5 mg of the original tissue weight, [$^{125}$I]Ang II (70 000 cpm, 0.03 nM) and variable concentrations of test substance. Samples were incubated at 25° C. for 1 h, and binding was terminated by filtration through Whatman GF/B glass-fiber filter sheets using a Brandel cell harvester. The filters were washed with 4×2 mL of Tris-HCl (pH 7.4) and transferred to tubes. The radioactivity was measured in a gamma counter. The characteristics of the Ang II binding $AT_1$ receptor were determined by using six different concentrations (0.03-5 nmol/L) of the labeled [$^{125}$I]AngII. Non-specific binding was determined in the presence of 1 μM Ang II. The specific binding was determined by subtracting the non-specific binding from the total bound [$^{125}$I]AngII. The dissociation constant ($K_d$=1.7±0.1 nM, [L]=0.057 nM) was determined by Scatchard analysis of data obtained with Ang II by using GraFit (Erithacus Software, UK). The binding data were best fitted with a one-site fit. All experiments were performed at least in triplicate.

Test B

Receptor Binding Assay Using Porcine Myometrial Membrane $AT_2$ Receptor

Myometrial membranes were prepared from porcine uteri according to the method by Nielsen et al (*Clin. Exp. Pharm. Phys.* (1997) 24, 309). Any possible interference that may be exhibited by binding of compound to AT1 receptors was blocked by addition of 1 μM of a selective AT1 inhibitor. Binding of [$^{125}$I]Ang II to membranes was conducted in a final volume of 0.5 mL containing 50 mM Tris-HCl (pH 7.4), 100 mM NaCl, 10 mM $MgCl_2$, 1 mM EDTA, 0.025% bacitracin, 0.2% BSA, homogenate corresponding to 10 mg of the original tissue weight, [$^{125}$I]Ang II (70 000 cpm, 0.03 nM) and variable concentrations of test substance. Samples were incubated at 25° C. for 1 h, and binding was terminated by filtration through Whatman GF/B glass-fiber filter sheets using a Brandel cell harvester. The filters were washed with 3×3 mL of Tris-HCl (pH 7.4) and transferred to tubes. The radioactivity was measured using a gamma counter. The characteristics of the Ang II binding $AT_2$ receptor was determined by using six different concentrations (0.03-5 nmol/L) of the labeled [$^{125}$I]Ang II. Non-specific binding was determined in the presence of 1 μM Ang II. The specific binding was determined by subtracting the non-specific binding from the total bound [$^{125}$I]Ang II. The dissociation constant ($K_d$=0.7±0.1 nM, [L]=0.057 nM) was determined by Scatchard analysis of data obtained with Ang II by using GraFit (Erithacus Software, UK). The binding data were best fitted with a one-site fit. All experiments were performed at least in triplicate.

Test C

Duodenal Mucosal Alkaline Secretion Assay

Compounds were exposed to the duodenal mucosa in barbiturate-anaesthetised rats prepared for in situ titration of duodenal mucosal alkaline secretion, according to the methodology described by Flemström et al in *Am. J. Physiol.* (1982) 243, G348.

The invention is illustrated by way of the following examples.

PREPARATION A 3-(4-Formylphenyl)-5-iso-butyl-N-tert-butylthiophene-2-sulfonamide (a) N-tert-Butylthiophene-2-sulfonamide Thiophene-2-sulfonyl chloride (15 g, 0.082 mol) was dissolved in $CHCl_3$ (200 mL) under $N_2$ atmosphere and then cooled to 0° C. tert-Butylamine (25.9 mL, 0.246 mol) dissolved in $CHCl_3$ (50 mL) was then added dropwise to the reaction mixture. The reaction mixture was stirred for 1 h at room temperature and then at reflux for 10 min. Toluene (700 mL) was added and the organic phase was washed with water (3×50 mL), dried, and concentrated in vacuo. The sub-title product was used without further purification in the next step.

¹H NMR (CDCl₃) δ 7.60 (1H, dd, J=1.3, 3.8 Hz), 7.53 (1H, dd, J=1.3, 5.0 Hz), 7.02 (1H, dd, J=5.0, 3.8 Hz), 5.13 (1H, m), 1.24 (9H, m).
¹³C NMR (CDCl₃) δ 145.0, 131.7, 131.2, 127.0, 55.1, 29.9.

(b) 5-iso-Butyl-N-tert-butylthiophene-2-sulfonamide

N-tert-Butylthiophene-2-sulfonamide (10 g, 0.046 mol, see step (a) above) was dissolved in THF (85 mL) under N₂ and then cooled to −78° C. n-BuLi (1.6 M, 76.9 mL, 0.12 mol) was added via a syringe. The reaction mixture was stirred at −78° C. for 30 min. and then at −40° C. for 2 h. Iodo-2-methylpropane (10.5 mL, 0.09 mol) was added dropwise to the reaction mixture. The reaction mixture was stirred overnight at room temperature. The reaction was quenched with NH₄Cl (aq.) and extracted with EtOAc. The combined organic phase was washed with brine, dried and concentrated in vacuo. The crude product was purified by column chromatography (Hex/EtOAc (10:1)) to give the sub-title compound in 55% yield (7.0 g, 0.025 mol).
¹H NMR (CDCl₃) δ 7.43 (1H, d, J=3.6 Hz), 6.67 (1H, d, J=3.8 Hz), 4.83 (1H, m), 2.67 (2H, d, J=7 Hz), 1.88 (1H, m), 1.26 (9H, m), 0.93 (6H, J=6.6 Hz).
¹³C NMR (CDCl₃) δ 145.0, 131.7, 131.2, 127.0, 55.1, 29.9.

(c) 5-iso-Butyl-2-(N-tert-butylaminosulfonyl) thiophene-3-boronic acid 5-iso-Butyl-N-tert-butylthiophene-2-sulfonamide (10.6 g, 0.039 mol, see step (b) above) was dissolved in THF (165 mL) under N₂ and then cooled to −78° C. n-BuLi (1.6 M, 60.19 mL, 0.096 mol) was added via a syringe. The reaction mixture was stirred at −20° C. for 4 h. Tri-iso-propylborate (13.3 mL, 0.058 mol) was then added via a syringe and the reaction mixture was stirred overnight at room temperature. The reaction was quenched with HCl (2 M, 20 mL). The organic phase was separated and the water phase was extracted with EtOAc (3×100 mL). The combined organic phase was washed with brine, dried and concentrated in vacuo. The product was used without further purification.
MS (ESI⁺) m/z: 236.8.

(d) 3-(3-Formylphenyl)-5-iso-butyl-N-tert-butylthiophene-2-sulfonamide

Palladium acetate (84.6 mg, 0.38 mmol) and triphenylphosphine (0.40 g, 1.52 mmol) in DME (5 mL) were stirred for 30 min under N₂(g). The catalyst was then transferred into a nitrogen-flushed mixture of 5-iso-butyl-2-(N-tert-butylaminosulfonyl)thiophene-3-boronic acid (4.0 g, 12.56 mmol, see step (c) above), 3-bromobenzaldehyde (2.96 g, 25.12 mmol) and potassium carbonate (5.21 g, 37.7 mmol) in a solvent mixture of DME (28 mL), ethanol (8 mL), and water (12 mL). After stirring for 20 h at reflux under a N₂ atmosphere, the reaction mixture was diluted with NaOH (1M solution, 50 mL) followed by ethyl acetate (150 mL). The organic layer was washed with water, and brine, dried (over anhydrous MgSO₄), concentrated in vacuo, and the residue subjected to flash chromatography (20% ethyl acetate in petroleum ether, 230-400 mesh) to afford the title compound as colourless solid (3.9 g, 10.3 mmol, 82%).
m.p. 96-98° C.
IR (neat, cm⁻¹) ν 2960, 1701, 1391, 1319, 1144, 1052
¹H NMR (CDCl₃) δ 0.98 (d, 6H, J=6.6 Hz), 1.03 (s, 9H), 1.93 (m, 1H), 2.69 (d, 2H, J=6.6 Hz), 4.22 (br s, 1H), 6.79 (s, 1H), 7.61 (t, 1H, J=7.92 Hz), 7.88-7.98 (m, 2H), 8.04 (t, 1H, J=1.65 Hz), 10.05 (s, 1H).
¹³C NMR (CDCl₃) δ 22.12, 29.58, 30.52, 39.14, 54.75, 128.89, 129.10, 129.39, 130.01, 135.18, 135.88, 136.31, 137.04, 141.82, 148.90, 191.95.
MS (ESI⁺) m/z: 380.0 (M⁺+1).
Anal. Calcd for C₁₉H₂₅NO₃S₂: C, 60.1; H, 6.6; N, 3.7; Found C, 60.4; H, 6.7; N, 3.7.

EXAMPLES 1 TO 18

General Procedure
Step 1: The appropriate amine (1.1 eqv., 0.09 mmol, see below) was added to a solution of 3-(3-formylphenyl)-5-iso-butyl-N-tert-butylthiophene-2-sulfonamide (30 mg, 0.08 mmol, see Preparation A above) in methanol (1 mL) in a sample vial (5 mL size). After being stirred for 30 min, sodium borohydride (3.0 mg, 0.08 mmol) was added and the stirring continued for 30 min. The mixture was acidified with conc. HCl (0.2 mL), stirred for 5 min, neutralised with saturated NaHCO₃ solution (~0.5 mL) and diluted with ethyl acetate (10 mL). The contents were poured into diatomaceous earth (liquid-liquid extraction cartridge) in a polypropylene column (packed for 7 cm in a column of 24 mL capacity) and eluted with ethyl acetate (30 mL). Concentration under vacuum afforded the crude product.
Step 2: The product from step 1 was dissolved in dry DCM (1.5 mL) in a sample vial (5 mL size). Triethylamine (0.022 mL, 0.16 mmol) and the appropriate acid chloride or alkyl chloroformate (1.1 equiv., 0.09 mmol, see below) were then added sequentially (optionally in the presence of a catalytic amount of DMAP). The sample vial was tightly closed and the mixture was stirred for 2 hours. Water (0.6 mL) was added, followed by ethyl acetate (5 mL). The mixture was then filtered through diatomaceous earth (packed for 7 cm in the column of 24 mL capacity) on elution with ethyl acetate (20 mL). Concentration in vacuo afforded the crude product.
Step 3: The mixture of the product from step 2 and anisole (~2 drops) in trifluoroacetic acid (3 mL) in a sample vial (5 mL size) was stirred overnight. After the removal of the solvent in vacuo, the residue was dissolved in acetonitrile (2×6 mL) and evaporated.
Step 4: To a mixture of the product from step 3 in dry DCM (1.5 mL), pyrrolidinopyridine (1.2 mg, 0.008 mmol) and triethylamine (34 μL, 0.24 mmol), n-butyl chloroformate (20 μL, 0.16 mmol) were sequentially added. The solution was stirred for 2 h, concentrated in vacuo and the crude product purified by LCMS (Liquid Chromatography Mass Spectrum; acetonitrile gradient, reverse phase) to afford the title products indicated below.

Example 1

N-Butyloxycarbonyl-3-[3-(N-benzyl-2-thiophenecarbonylaminomethyl)phenyl]-5-iso-butylthiophene-2-sulfonamide The title compound was synthesised in accordance with the General Procedure using benzylamine and 2-thiophenecarboxyl chloride. The crude product was purified by LCMS (55% to 82% aqueous acetonitrile, 40 min., reverse phase) to afford a colourless syrup (43 mg, 86%).
IR (neat, cm⁻¹) ν 3062, 2959, 1748, 1604, 1458.
¹H NMR (CDCl₃) δ 0.86 (t, J=7.26 Hz, 3H), 0.99 (d, J=6.6 Hz, 6H), 1.26 (m, 2H), 1.51 (m, 2H), 1.96 (m, 1H), 2.71 (d, J=6.9 Hz, 2H), 4.04 (t, J=6.6 Hz, 2H), 4.67 (br s, 2H), 4.91 (br s, 2H), 6.86 (s, 1H), 6.94 (t, J=4.3 Hz, 1H), 7.18 (dt, J=1.3 Hz, J=4.3 Hz, 1H), 7.31-7.46 (m, 10H), 8.04 (br s, 1H).

$^{13}$C NMR (CDCl$_3$) δ 13.6, 18.7, 22.2, 29.8, 30.4, 39.3, 50.3, 53.4, 66.5, 126.6, 126.9, 127.8, 128.3, 129.1, 129.6, 130.1, 130.6, 131.5, 134.2, 136.0, 136.3, 136.9, 144.6, 150.9, 151.0, 166.1.

MS (ESI$^+$) m/z: 625.1 (M$^+$+1).

Anal. Calcd. for C$_{32}$H$_{36}$N$_2$O$_5$S$_3$: C, 61.51; H, 5.81; N, 4.48; Found: C, 61.35; H, 5.81; N, 4.34.

Example 2

N-Butyloxycarbonyl-3-[3-(N-benzylpentylamidomethyl)phenyl]-5-iso-butylthiophene-2-sulfonamide The title compound was synthesised in accordance with the General Procedure using benzylamine and valeryl chloride. The crude product obtained from the final step was purified by LCMS (58% to 88% aqueous acetonitrile, 45 min., reverse phase) to afford a colourless syrup (30 mg, 63%).

IR (neat, cm$^{-1}$) ν 2959, 1748, 1620, 1466.

$^1$H NMR (CDCl$_3$) δ 0.88 (t, J=7.3 Hz, 6H), 0.99 (d, J=6.6 Hz, 6H), 1.20-1.39 (m, 4H), 1.48-1.77 (m, 4H), 1.95 (m, 1H), 2.44 (t, J=7.9 Hz, 2H), 2.70 (d, J=6.9 Hz, 2H), 4.02-4.11 (m, 2H), 4.46-4.70 (m, 4H), 6.79-6.86 (m, 1H), 7.08-7.41 (m, 9H), 7.93 (s, 1H).

$^{13}$C NMR (CDCl$_3$): 13.7, 13.8, 18.8, 22.3, 22.4, 30.5, 33.1, 39.3, 50.1, 51.8, 66.2, 126.5, 127.3, 127.8, 128.6, 129.0, 130.2, 131.6, 134.0, 136.1, 137.1, 144.6, 151.0, 175.7.

MS (ESI$^+$) m/z: 599.5 (M$^+$+2).

Anal. Calcd. for C$_{32}$H$_{42}$N$_2$O$_5$S$_2$: C, 64.2; H, 7.1; N, 4.7; Found C, 64.3; H, 7.2; N, 4.7.

Example 3

N-Butyloxycarbonyl-3-[3-(N-acetylbenzylaminomethyl)phenyl]-5-iso-butylthiophene-2-sulfonamide The title compound was synthesised in accordance with the General Procedure using benzylamine and acetyl chloride. The crude product obtained from the final step was purified by LCMS (50% to 80% aqueous acetonitrile, 45 min., reverse phase) to afford a colourless syrup (27 mg, 61%).

IR (neat, cm$^{-1}$) ν 2961, 1748, 1627, 1466.

$^1$H NMR (CDCl$_3$) δ 0.83 (t, J=7.3 Hz, 3H), 0.96 (d, J=6.6 Hz, 6H), 1.21 (m, 2H), 1.48 (m, 2H), 1.92 (m, 1H), 2.21 and rotamer at 2.16 (s, 3H), 2.67 (d, J=6.9 Hz, 2H), 3.99 and rotamer at 4.06 (t, J=6.6 Hz, 2H), 4.45-4.63 (m, 4H), 6.75-6.84 (m, 1H), 7.04-7.39 (m, 8H), 7.85 (s, 1H), 10.01 (s, 1H).

$^{13}$C NMR (CDCl$_3$) δ 13.6, 18.7, 22.0, 22.2, 30.4, 29.3, 48.6, 49.8, 50.7, 52.7, 66.3, 66.8, 126.5, 126.9, 127.2, 127.7, 127.8, 139.2, 128.3, 128.6, 129.0, 129.3, 133.9, 135.9, 136.6, 136.9, 144.4, 150.8, 151.0, 173.5.

MS (ESI$^+$) m/z: 557.3 (M$^+$+1).

Anal. Calcd. for C$_{29}$H$_{36}$N$_2$O$_5$S$_2$.1/2H$_2$O: C, 61.6; H, 6.6; N, 5.0; Found: C, 61.7; H, 7.0; N, 5.1.

Example 4

N-Butyloxycarbonyl-3-[3-(N-p-tolylbenzylamidomethyl)phenyl]-5-iso-butylthiophene-2-sulfonamide The title compound was synthesised in accordance with the General Procedure using p-tolylamine and benzoyl chloride. The crude product obtained from the final step was purified by LCMS (58% to 88% aqueous acetonitrile, 50 min., reverse phase) to afford a colourless syrup (30 mg, 61%).

IR (neat, cm$^{-1}$) ν 2959, 1749, 1626, 1448.

$^1$H NMR (CDCl$_3$) δ 0.85 (t, J=7.3 Hz, 3H), 1.0 (d, J=6.6 Hz, 6H), 1.24 (m, 2H), 1.51 (m, 2H), 1.96 (m, 1H), 2.26 (s, 3H), 2.71 (d, J=6.9 Hz, 2H), 4.04 (t, J=6.6 Hz, 2H), 5.07 (s, 2H), 6.84-7.01 (m, 6H), 7.01-7.38 (m, 8H), 8.17 (s, 1H).

$^{13}$C NMR (CDCl$_3$) δ 13.6, 18.8, 29.9, 22.2, 304.5, 39.3, 55.3, 66.3, 113.8, 127.5, 127.6, 127.8, 128.0, 128.2, 128.4, 129.0, 130.9, 131.5, 133.9, 135.3, 136.5, 136.8, 140.7, 144.6, 150.9, 151.01, 171.9.

MS (ESI$^+$) m/z: 619.2 (M$^+$+1).

Anal. Calcd. for C$_{34}$H$_{38}$N$_2$O$_5$S$_2$: C, 65.99; H, 6.19; N, 4.53; Found: C, 65.82; H, 6.29; N, 4.40.

Example 5

N-Butyloxycarbonyl-3-[3-(N-acetyl-p-tolylaminomethyl)phenyl]-5-iso-butylthiophene-2-sulfonamide The title compound was synthesised in accordance with the General Procedure using p-tolylamine and acetyl chloride. The crude product obtained from the final step was purified by LCMS (50% to 75% aqueous acetonitrile, 50 min., reverse phase) to afford a colourless syrup (27 mg, 62%).

IR (neat, cm$^{-1}$) ν 2959, 1748, 1628, 1458, 1344.

$^1$H NMR (CDCl$_3$) δ 0.89 (t, J=7.6 Hz, 3H), 1.0 (d, J=6.6 Hz, 6H), 1.29 (m, 2H), 1.56 (m, 2H), 1.93-2.01 (m, 4H), 2.36 (s, 3H), 2.71 (d, J=6.9 Hz, 2H), 4.07 (t, J=6.6 Hz, 2H), 4.84 (s, 2H), 6.89-6.97 (m, 4H), 7.17 (d, J=8.25 Hz, 2H), 7.22-7.32 (m, 2H), 8.05 (s, 1H).

$^{13}$C NMR (CDCl$_3$) δ 13.7, 18.8, 21.1, 22.3, 23.0, 30.5, 39.3, 54.1, 66.3, 127.3, 127.7, 128.1, 130.0, 130.3, 131.6, 133.9, 137.0, 138.1, 140.4, 144.5, 151.05, 173.3.

MS (ESI$^+$) m/z: 557.3 (M$^+$+1).

Anal. Calcd. for C$_{29}$H$_{36}$N$_2$O$_5$S$_2$: C, 62.56; H, 6.52; N, 5.03 Found: C, 62.39; H, 6.57; N, 4.92.

Example 6

N-Butyloxycarbonyl-3-{3-[N-(pyridin-3-ylmethyl)benzylamidomethyl]phenyl}-5-iso-butylthiophene-2-sulfonamide The title compound was synthesised in accordance with the General Procedure using 3-picolylamine and benzoyl chloride. The crude product obtained from the final step was purified by LCMS (55% to 85% aqueous acetonitrile, 45 min., reverse phase) to afford a colourless solid (32 mg, 65%).

m.p. 73-75° C.

IR (neat, cm$^{-1}$) ν 2960, 1740, 1635, 1412.

$^1$H NMR (CDCl$_3$) δ 0.89 (t, J=7.3 Hz, 3H), 0.97 (d, J=6.6 Hz, 6H), 1.31 (m, 2H), 1.59 (m, 2H), 1.91 (m, 1H), 2.67 (d, J=6.9 Hz, 2H), 4.11 (t, J=6.6 Hz, 2H), 4.74 (br m, 4H), 6.46-7.08 (br m, 4H), 7.20 (br s, 2H), 7.33-7.6 (m, 6H), 7.64-8.33 (m, 2H).

$^{13}$C NMR (CDCl$_3$) δ 13.6, 18.9, 22.2, 30.5, 30.6, 39.2, 47.9, 50.2, 52.3, 54.5, 66.0, 123.6, 126.8, 127.8, 128.7, 129.5, 129.8, 132.2, 132.7, 134.8, 135.6, 136.1, 137.1, 137.9, 145.0, 146.4, 147.2, 149.4, 150.5, 151.7, 172.5.

MS (ESI$^+$) m/z: 620.5 (M$^+$+1).

Anal. Calcd. for C$_{33}$H$_{37}$N$_3$O$_5$S$_2$. H$_2$0: C, 62.1; H, 6.2; N, 6.6 Found C, 62.0; H, 6.0; N, 6.2.

Example 7

N-Butyloxycarbonyl-3-{3-[N-acetyl(pyridin-3-ylmethyl)aminomethyl]phenyl}-5-iso-butylthiophene-2-sulfonamide The title compound was synthesised in accordance with the General Procedure using 3-picolylamine and acetyl chloride.

The crude product obtained from the final step was purified by LCMS (45% to 75% aqueous acetonitrile, 35 min., reverse phase) to afford a colourless syrup (26 mg, 61%).

IR (neat, cm$^{-1}$) ν 2960, 1745, 1651, 1466, 1427.

$^1$H NMR (CDCl$_3$) δ 0.86-1.01 (m, 10H), 1.30 (m, 2H), 1.57 (m, 2H), 1.93 (m, 1H), 2.31 (m, 3H), 2.69 (d, J=6.9 Hz, 2H), 4.09 (m, 2H), 4.63-4.75 (s, 4H), 6.52-6.61 (m, 1H), 6.74-7.32 (m, 7H), 7.50-7.91 (m, 1H).

$^{13}$C NMR (CDCl$_3$) δ 13.7, 18.9, 21.7, 22.0, 22.2, 30.5, 30.7, 39.2, 47.9, 50.3, 51.3, 53.8, 66.0, 66.2, 126.2, 127.6, 127.8, 127.9, 128.6, 129.0, 129.4, 131.9, 132.8, 134.5, 134.8, 136.2, 137.0, 138.0, 144.9, 150.5, 150.8, 151.3, 151.8, 170.8, 172.0.

MS (ESI$^+$) m/z: 558.4 (M$^+$+1).

Example 8

N-Butyloxycarbonyl-3-[3-(N-methylpentylamidomethyl)phenyl]-5-iso-butylthiophene-2-sulfonamide The title compound was synthesised in accordance with the General Procedure using methylamine and valeryl chloride. The crude product obtained from the final step was purified by LCMS (50% to 80% aqueous acetonitrile, 30 min., reverse phase) to afford a colourless syrup (24 mg, 58%).

IR (neat, cm$^{-1}$) ν 2960, 1748, 1628, 1466.

$^1$H NMR (CDCl$_3$) δ 0.84-0.99 (m, 12H), 1.17-1.72 (m, 8H), 1.93 (m, 1H), 2.39 (m, 2H), 2.70 (m, 2H), 2.97 and rotamer at 2.93 (s, 3H), 4.03 (m, 2H), 4.58 (m, 2H), 6.75 (m, 1H), 7.21 (m, 2H), 7.44 (m, 2H).

$^{13}$C NMR (CDCl$_3$) δ 13.6, 13.9, 18.7, 22.2, 22.6, 27.2, 27.5, 30.4, 30.5, 32.9, 33.2, 33.9, 35.2, 39.3, 50.9, 53.1, 66.7, 66.8, 126.2, 127.7, 128.6, 129.1, 129.4, 130.8, 133.0, 133.3, 137.4, 138.1, 146.1, 150.3, 151.3, 151.5, 173.6.

MS (ESI$^+$) m/z: 523.3 (M$^+$+1).

Anal. Calcd. for C$_{26}$H$_{38}$N$_2$O$_5$S$_2$: C, 59.74; H, 7.33; N, 5.36; Found: C, 59.49; H, 7.34; N, 5.46.

Example 9

N-Butyloxycarbonyl-3-[3-(N-acetylmethylaminomethyl)phenyl]-5-iso-butylthiophene-2-sulfonamide The title compound was synthesised in accordance with the General Procedure using methylamine and acetyl chloride. The crude product obtained from the final step was purified by LCMS (35% to 70% aqueous acetonitrile, 40 min., reverse phase) to afford a colourless syrup (24 mg, 65%).

IR (neat, cm$^{-1}$) ν 2959, 1747, 1620, 1466.

$^1$H NMR (CDCl$_3$) δ 0.86 (t, J=7.3 Hz, 3H), 0.99 (d, J=6.6 Hz, 6H), 1.25 (m, 2H), 1.51 (m, 2H), 1.95 (m, 1H), 2.17 and rotamer at 2.14 (s, 3H), 2.70 (d, J=7.3 Hz, 2H), 3.11 and rotamer at 3.08 (s, 3H), 4.01 and rotamer at 4.09 (t, J=6.9 Hz, 2H), 4.54 and rotamer at 4.59 (s, 2H), 6.88 and rotamer at 6.79 (s, 1H), 7.2-7.41 (m, 3H), 7.81 (s, 1H).

$^{13}$C NMR (CDCl$_3$) δ 13.6, 18.8, 22.2, 29.7, 30.5, 33.1, 34.4, 37.3, 39.3, 52.3, 54.1, 66.3, 66.8, 126.6, 126.9, 127.3, 127.5, 128.1, 128.9, 129.2, 131.6, 134.0, 136.9, 144.4, 150.9, 151.0, 173.0.

MS (ESI) m/z: 481.2 (M$^+$+1).

Anal. Calcd. for C$_{23}$H$_{32}$N$_3$O$_5$S$_2$: C, 57.48; H, 6.71; N, 5.83; Found: C, 58.0; H, 7.0; N, 5.9.

Example 10

N-Butyloxycarbonyl-3-[3-(N-ethyl-2-thiophenecarbonylaminomethyl)phenyl]-5-iso-butylthiophene-2-sulfonamide The title compound was synthesised in accordance with the General Procedure using ethylamine and 2-thiophenecarboxyl chloride. The crude product obtained from the final step was purified by LCMS (50% to 80% aqueous acetonitrile, 30 min., reverse phase) to afford a colourless syrup (22 mg, 48%).

IR (neat, cm$^-$) ν 2960, 1748, 1604, 1436.

$^1$H NMR (CDCl$_3$) δ 0.86 (t, J=7.6 Hz, 3H), 0.98 (d, J=6.6 Hz, 6H), 1.17-1.29 (m, 5H), 1.49 (m, 2H), 1.94 (m, 1H), 2.71 (d, J=7.3 Hz, 2H), 3.57 (q, J=6.9 Hz, 2H), 4.02 (t, J=6.6 Hz, 2H), 4.79 (s, 2H), 6.77 (s, 1H), 7.01 (m, 1H), 7.31-7.35 (m, 3H), 7.44-7.48 (m, 3H).

$^{13}$C NMR (CDCl$_3$) δ 13.6, 18.7, 22.2, 30.4, 30.5, 39.3, 42.7, 66.8, 126.9, 127.1, 128.6, 129.1, 129.3, 130.6, 133.2, 137.6, 137.8, 146.1, 150.1, 151.5, 164.6.

MS (ESI$^+$) m/z: 563.3 (M$^+$+1).

Anal. Calcd. for C$_{27}$H$_{34}$N$_2$O$_5$S$_3$: C, 57.62; H, 6.09; N, 4.98; Found: C, 57.8; H, 6.24; N, 5.14.

Example 11

N-Butyloxycarbonyl-3-[3-(N-acetylethylaminomethyl)phenyl]-5-iso-butylthiophene-2-sulfonamide The title compound was synthesised in accordance with the General Procedure using ethylamine and acetyl chloride. The crude product obtained from the final step was purified by LCMS (45% to 75% aqueous acetonitrile, 45 min.) to afford a colourless syrup (31 mg, 80%).

IR (neat, cm$^{-1}$) ν 2960, 1748, 1619, 1459.

$^1$H NMR (CDCl$_3$) δ 0.80 (t, J=7.3 Hz, 3H), 0.94 (d, J=6.6 Hz, 6H), 1.07-1.24 (m, 5H), 1.42 (m, 2H), 1.90 (m, 1H), 2.15 and rotamer at 2.03 (s, 3H), 2.65 (d, J=6.9 Hz, 2H), 3.89 (q, J=7.3 Hz, 2H), 3.91 and rotamer at 4.04 (t, J=6.6 Hz, 2H), 4.49 and rotamer at 4.52 (s, 2H), 6.84 (m, 1H), 7.16-7.33 (m, 3H), 7.75 (s, 1H).

$^{13}$C NMR (CDCl$_3$) δ 12.8, 13.6, 13.9, 18.7, 21.6, 22.2, 29.8, 30.4, 33.1, 39.2, 41.1, 44.7, 49.8, 51.2, 66.1, 66.6, 126.4, 127.0, 127.1, 129.1, 128.2, 128.6, 129.0, 131.6, 133.7, 134.6, 137.1, 137.5, 144.1, 145.7, 150.6, 150.7, 151.7, 152.1, 172.1, 172.7.

MS (ESI$^+$) m/z: 495.2 (M$^+$+1).

Anal. Calcd. for C$_{24}$H$_{34}$N$_2$O$_5$S$_2$: C, 58.3; H, 6.9; N, 5.7; Found: C, 58.3; H, 7.1; N, 5.8.

Example 12

N-Butyloxycarbonyl-3-[3-(N-ethyloxycarbonylmethylaminomethyl)phenyl]-5-iso-butylthiophene-2-sulfonamide The title compound was synthesised in accordance with the General Procedure using methylamine and ethyl chloroformate. The crude product obtained from the final step was purified by LCMS (45% to 75% aqueous acetonitrile, 40 min., reverse phase) to afford a colourless oil (24 mg, 60%).

IR (neat, cm$^{-1}$) ν 2959, 1750, 1671, 1458.

$^1$H NMR (CDCl$_3$) δ 0.86 (t, J=7.3 Hz, 3H), 0.99 (d, J=6.6 Hz, 6H), 1.16-1.29 (m, 5H), 1.46 (m, 2H), 1.95 (m, 1H), 2.70

(d, J=7.3 Hz, 2H), 3.04 (s, 3H), 3.97 (t, J=6.6 Hz, 2H), 4.20 (q, J=7.3 Hz, 2H), 4.42 (s, 2H), 6.86 (s, 1H), 7.24-7.39 (m, 4H), 7.82 (s, 1H).

$^{13}$C NMR (CDCl$_3$) δ 13.6, 14.5, 18.7, 22.2, 30.4, 35.5, 39.3, 53.4, 62.2, 66.2, 127.4, 127.6, 128.3, 128.5, 129.3, 131.6, 134.0, 137.4, 144.4, 150.7, 150.9, 157.7.

MS (ESI$^+$) m/z: 511.3 (M$^+$+1).

Anal. Calcd. for C$_{24}$H$_{34}$N$_2$O$_6$S$_2$: C, 56.5; H, 6.7; N, 5.5; Found: C, 56.61; H, 6.78; N, 5.39.

Example 13

N-Butyloxycarbonyl-3-(3-{[(ethoxycarbonylcarbonyl)methylamino]methyl}-phenyl)-5-iso-butylthiophene-2-sulfonamide The title compound was synthesised in accordance with the General Procedure using methylamine and ethyloxalyl chloride. The crude product obtained from the final step was purified by LCMS (45% to 75% aqueous acetonitrile, 40 min., reverse phase) to afford a colourless oil (31 mg, 73%).

IR (neat, cm$^{-1}$) ν 2960, 2159, 2032, 1977, 1747, 1658, 1446.

$^1$H NMR (CDCl$_3$) δ 0.87 (t, J=7.3 Hz, 3H), 0.98 (dd, J=2.0 Hz, J=6.6 Hz, 6H), 1.18-1.41 (m, 5H), 1.53 (m, 2H), 1.94 (m, 1H), 2.70 (dd, J=1.7 Hz, J=6.9 Hz, 2H), 3.04 and rotamer at 2.91 (s, 3H), 4.05 (t, J=6.6 Hz, 2H), 4.35 (dq, J=2.3 Hz, J=6.9 Hz, 2H), 4.58 and rotamer at 4.49 (s, 2H), 6.80 and rotamer at 6.78 (s, 1H), 7.26-7.44 (m, 3H), 7.62 (s, 1H).

$^{13}$C NMR (CDCl$_3$) δ 13.6, 13.9, 18.7, 22.2, 30.5, 32.2, 35.5, 39.3, 50.8, 53.5, 62.4, 62.7, 66.6, 66.7, 127.6, 128.2, 128.3, 128.4, 128.6, 128.7, 129.0, 129.5, 131.1, 134.6, 134.8, 135.2, 135.5, 145.3, 145.5, 150.4, 150.6, 151.5, 151.6, 161.7, 162.0, 162.5, 163.5.

MS (ESI$^+$) m/z: 539.3 (M$^+$+1).

Anal. Calcd. for C$_{25}$H$_{34}$N$_2$O$_7$S$_2$: C, 55.74; H, 6.36; N, 5.20; Found: C, 55.63; H, 6.39; N, 5.10.

Example 14

N-Butyloxycarbonyl-3-[3-(N-(2,2,2-trifluoroethyl)cyclopropylcarboxylamino-methyl)phenyl]-5-iso-butylthiophene-2-sulfonamide The title compound was synthesised in accordance with the General Procedure using trifluoromethylamine and cyclopropanecarbonyl chloride. The crude product obtained from the final step was purified by LCMS (55% to 85% aqueous acetonitrile, 40 min., reverse phase) to afford a colourless syrup (24 mg, 53%).

IR (neat, cm$^{-1}$) ν 2961, 1750, 1639, 1458, 1347.

$^1$H NMR (CDCl$_3$) δ 0.80-1.01 (m, 11H), 1.08-1.34 (m, 4H), 1.48-1.77 (m, 4H), 1.95 (m, 1H), 2.70 (d, J=6.9 Hz, 2H), 4.02-4.20 (m, 4H), 4.63-4.92 (m, 2H), 6.78-6.83 (m, 1H), 7.24-7.44 (m, 3H), 7.82 (br s, 1H).

$^{13}$C NMR (CDCl$_3$) δ 8.6, 8.9, 11.8, 13.6, 18.8, 22.3, 30.5, 39.3, 45.9, 46.5, 48.3, 48.9, 49.4, 49.8, 51.6, 66.4, 67.0, 122.3, 126.4, 126.8, 127.2, 127.8, 127.9, 128.4, 128.6, 129.0, 130.9, 131.5, 134.3, 134.9, 136.2, 144.8, 146.0, 150.3, 150.7, 151.3, 152.1, 175.9.

MS (ESI$^+$) m/z: 575.3 (M$^+$+1).

Anal. Calcd. for C$_{26}$H$_{33}$F$_3$N$_2$O$_5$S$_2$.1/2H$_2$O: C, 53.5; H, 5.87; N, 4.8; Found: C, 53.5; H, 6.2; N, 4.8.

Example 15

N-Butyloxycarbonyl-3-[3-(acetyl-2,2,2-trifluoroethylaminomethyl)phenyl]-5-iso-butylthiophene-2-sulfonamide The title compound was synthesised in accordance with the General Procedure using trifluoroethylamine and acetyl chloride. The crude product obtained from the final step was purified by LCMS (45% to 75% aqueous acetonitrile, 40 min., reverse phase) to afford a colourless syrup (18 mg, 41%).

IR (neat, cm$^{-1}$) ν 2961, 1750, 1650, 1466, 1437.

$^1$H NMR (CDCl$_3$) δ 0.84-1.02 (m, 9H), 1.26 (m, 2H), 1.51 (m, 2H), 1.95 (m, 1H), 2.21-2.26 (m, 3H), 2.71 (m, 2H), 3.88-4.13 (m, 4H), 4.69-4.74 (m, 2H), 6.79-6.87 (m, 1H), 7.21-7.40 (m, 4H), 7.72 (s, 1H).

$^{13}$C NMR (CDCl$_3$) δ 13.6, 18.8, 21.7, 21.9, 22.3, 30.5, 39.3, 49.6, 50.1, 50.6, 52.4, 66.5, 67.0, 122.1, 126.2, 126.7, 127.6, 128.3, 128.6, 128.9, 131.4, 134.2, 135.0, 135.6, 136.0, 144.5, 145.8, 150.6, 151.3, 173.2, 173.7.

MS (ESI$^+$) m/z: 549.2 (M$^+$+1).

Anal. Calcd. for C$_{24}$H$_{31}$F$_3$N$_2$O$_5$S$_2$: C, 52.54; H, 5.70; N, 5.11; Found: C, 52.73; H, 5.83; N, 4.99.

Example 16

N-Butyloxycarbonyl-3-[3-(N-methyl-2-thiophenecarbonylaminomethyl)phenyl]-5-iso-butylthiophene-2-sulfonamide The title compound was synthesised in accordance with the General Procedure using ethylamine and 2-thiophenecarboxyl chloride. The crude product obtained from the final step was purified by LCMS (45% to 75% aqueous acetonitrile, 40 min., reverse phase) to afford a colourless syrup (18 mg, 42%).

IR (neat, cm$^{-1}$) ν 2959, 1748, 1597, 1458, 1345.

$^1$H NMR (CDCl$_3$) δ 0.84 (t, J=7.3 Hz, 3H), 0.99 (d, J=6.6 Hz, 6H), 1.22 (m, 2H), 1.46 (m, 2H), 1.95 (m, 1H), 2.70 (d, J=6.6 Hz, 2H), 3.36 (br s, 3H), 3.99 (t, J=6.6 Hz, 2H), 4.71 (s, 2H), 6.85 (s, 1H), 7.04 (t, J=4.0 Hz, 1H), 7.29-7.48 (m, 6H), 7.93 (br s, 1H).

$^{13}$C NMR (CDCl$_3$) δ 13.6, 18.7, 22.2, 30.4, 38.6, 39.3, 53.5, 66.4, 126.8, 127.7, 128.5, 129.8, 130.4, 131.6, 134.2, 136.6, 137.1, 144.5, 150.8, 151.0, 165.4.

MS (ESI$^+$) m/z: 549.1 (M$^+$+1).

Anal. Calcd. for C$_{26}$H$_{32}$N$_2$O$_5$S$_3$: C, 56.91; H, 5.88; N, 5.10; Found: C, 56.74; H, 5.94; N, 4.96.

Example 17

N-Butyloxycarbonyl-3-{3-[(2-thiophenesulphonyl)ethylaminomethyl]phenyl}-5-iso-butylthiophene-2-sulfonamide The title compound was synthesised in accordance with the General Procedure using the appropriate amine (ethylamine) and the appropriate sulfonyl chloride instead of the acid chloride (thiophenesulfonyl chloride). The crude product obtained from the final step was purified by LCMS (50% to 75% aqueous acetonitrile, 45 min., reverse phase) to afford a colourless syrup (27 mg, 57%).

IR (neat, cm$^{-1}$) ν 3240, 2960, 1750, 1450, 1346.

¹H NMR (CDCl₃) δ 0.86 (t, J=7.3 Hz, 3H), 0.99 (d, J=6.6 Hz, 6H), 1.06 (t, J=6.9 Hz, 3H), 1.26 (m, 2H), 1.52 (m, 2H), 1.95 (m, 1H), 2.71 (d, J=7.3 Hz, 2H), 3.30 (q, J=7.3 Hz, 2H), 4.04 (t, J=6.6 Hz, 2H), 4.33 (s, 2H), 6.79 (s, 1H), 7.11 (dd, J=3.6 Hz, J=5.0 Hz, 1H), 7.29-7.41 (m, 3H), 7.57-7.66 (m, 3H).

¹³C NMR (CDCl₃) δ 13.4, 13.6, 18.7, 22.2, 29.8, 30.3, 30.4, 39.3, 43.7, 66.7, 127.4, 128.0, 128.1, 128.5, 128.8, 131.0, 131.7, 132.1, 136.9, 139.7, 145.6, 150.5, 151.4.

MS (ESI⁺) m/z: 599 (M⁺+1).

Anal. Calcd. for C₂₆H₃₄N₂O₆S₄: C, 52.15; H, 5.72; N, 4.68; Found: C, 52.0; H, 5.8; N, 5.0.

Example 18

N-Butyloxycarbonyl-3-[3-(formyl-N-methylaminomethyl)phenyl]-5-iso-butylthiophene-2-sulfonamide A mixture of 3-(3-methylaminomethylphenyl)-5-iso-butyl-N-tert-butylthiophene-2-sulfonamide (50 mg, 0.13 mmol, prepared in accordance with Step 1 of the General Procedure, employing methylamine) and ammonium formate (0.4 g, 6.35 mmol) in CH₃CN (2 mL) was refluxed overnight, then cooled to room temperature and partitioned between ethyl acetate (20 mL) and water (20 mL). The organic layer was washed with water and brine, dried over anhydrous MgSO₄ and concentrated in vacuo to afford the crude product, which was purified by circular chromatography (1 mm thickness layer, silica gel 60, 60% ethyl acetate in pet. ether) to afford the pure product as a colourless syrup which was dissolved in trifluoroacetic acid (5 mL). Anisole (0.1 mL) was then added. The mixture was stirred overnight at room temperature, evaporated and co-evaporated with acetonitrile (2×6 mL). The residue was dissolved in CH₂Cl₂ (2.5 mL), after which triethylamine (0.07 mL, 0.5 mmol), and n-butyl chloroformate (0.033 mmol) were successively added. The mixture was stirred for 2 h, concentrated in vacuo and purified by preparative LCMS (40% to 70% gradient elution of aqueous acetonitrile, 45 min.) to afford the title compound as a colourless syrup (50 mg, 82%).

IR (neat, cm⁻¹) ν 2960, 1746, 1656, 1466.

¹H NMR (CDCl₃) δ 0.80 (t, J=7.3 Hz, 3H), 0.91 (d, J=6.6 Hz, 6H), 1.19 (m, 2H), 1.46 (m, 2H), 1.87 (m, 1H), 2.62 (d, J=6.9 Hz, 2H), 2.92 and rotamer at 2.70 (s, 3H), 3.98 (t, J=6.9 Hz, 2H), 4.41 and rotamer at 4.31 (s, 2H), 6.75 and rotamer at 6.68 (s, 1H), 7.12-7.33 (m, 3H), 7.58 (s, 1H), 8.0 (m, 1H).

¹³C NMR (CDCl₃) δ 13.6, 18.8, 22.2, 29.6, 30.4, 35.2, 39.3, 48.8, 53.4, 66.5, 66.8, 127.4, 127.7, 127.9, 128.4, 128.5, 128.7, 129.2, 129.5, 131.2, 131.5, 134.4, 134.7, 135.7, 144.9, 145.7, 150.5, 150.8, 151.3, 151.5, 163.2, 163.7.

MS (ESI⁺) m/z: 467.3 (M⁺+1).

Anal. Calcd. for C₂₂H₃₀N₂O₅S₂: C, 56.63; H, 6.48; N, 6.0; Found: C, 56.75; H, 6.61; N, 5.99.

Example 19

Title compounds of the Examples were tested in Tests A and B above and were found to exhibit an affinity for AT2 receptors of less than Ki=50 nM and an affinity for AT1 receptors of Ki=1 μM or greater.

Example 20

Title compounds of the Examples are tested in Test C above and are found to stimulate markedly mucosal alkalisation. This effect is blocked by co-administration of the selective AT2 receptor antagonist PD123319 (Sigma Chemical Company).

The invention claimed is:

1. A compound of formula I,

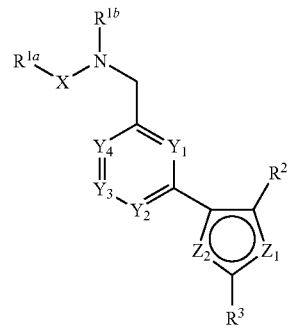

wherein

X represents —O—, —C(O)— or —S(O)₂—;

R$^{1a}$ and R$^{1b}$ independently represent H, C$_{1-6}$ alkyl, C$_{1-6}$ alkoxy-C$_{1-6}$ alkyl, Ar¹, Het¹, C$_{1-3}$ alkyl-Ar², C$_{1-3}$ alkyl-Het², C$_{1-3}$ alkoxy-Ar³ or C$_{1-3}$ alkoxy-Het³; or, in the case where X represents —C(O)—, R$^{1a}$ may also represent C$_{1-6}$ alkoxy, —O—Ar⁴, —C(O)—C$_{1-6}$ alkoxy, —C(O)—O—Ar⁵ or —C(O)—O-Het⁴;

Ar¹, Ar², Ar³, Ar⁴ and Ar⁵ each independently represent a C$_{6-10}$aryl group, which group is optionally substituted by one or more substituents selected from =O, —OH, cyano, halo, nitro, C$_{1-6}$ alkyl (optionally terminated by —N(H)C(O)OR$^{11a}$), C$_{1-6}$ alkoxy, phenyl, —N(R$^{12a}$)R$^{12b}$, —C(O)R$^{12c}$, —C(O)OR$^{12d}$, —C(O)N(R$^{12e}$)R$^{12f}$, N(R$^{12g}$)C(O)R$^{12h}$, —N(R$^{12i}$)C(O)N(R$^{12j}$)R$^{12k}$, —N(R$^{12m}$)S(O)₂R$^{11b}$, —S(O)$_n$R$^{11c}$, —OS(O)₂R$^{11d}$ and —S(O)₂N(R$^{12n}$)R$^{12p}$;

Het¹, Het², Het³ and Het⁴ each independently represent a four- to twelve-membered heterocyclic group containing one or more heteroatoms selected from oxygen, nitrogen and/or sulfur, which heterocyclic group is optionally substituted by one or more substituents selected from =O, —OH, cyano, halo, nitro, C$_{1-6}$ alkyl (optionally terminated by —N(H)C(O)OR$^{11a}$), C$_{1-6}$ alkoxy, phenyl, —N(R$^{12a}$)R$^{12b}$, —C(O)R$^{12c}$, —C(O)OR$^{12d}$, —C(O)N(R$^{12e}$)R$^{12f}$, —N(R$^{12g}$)C(O)R$^{12h}$, —N(R$^{12i}$)C(O)N(R$^{12j}$)R$^{12k}$, —N(R$^{12m}$)S(O)₂R$^{11b}$, —S(O)$_n$R$^{11c}$, —OS(O)₂R$^{11d}$ and —S(O)₂N(R$^{12n}$)R$^{12p}$;

R$^{11a}$ to R$^{11d}$ independently represent C$_{1-6}$ alkyl;

R$^{12a}$ to R$^{12p}$ independently represent H or C$_{1-6}$ alkyl;

n represents 0, 1 or 2;

Y₁, Y₂, Y₃ and Y₄ independently represent —CH— or —CF—;

Z₁ represents —CH—, —O—, —S—, —N— or —CH=CH—;

Z₂ represents —CH—, —O—, —S— or —N—;

provided that:

(a) Z₁ and Z₂ are not the same;

(b) when Z₁ represents —CH=CH—, then Z₂ may only represent —CH— or —N—; and (c) other than in the specific case in which Z₁ represents —CH=CH—, and Z₂ represents —CH—, when one of Z₁ and Z₂ represents —CH—, then the other represents —O— or —S—;

R² represents —S(O)₂N(H)C(O)R⁴, —S(O)₂N(H)S(O)₂R⁴, —C(O)N(H)S(O)₂R⁴, or, when $Z_1$ represents —CH=CH—, R² may represent —N(H)S(O)₂N(H)C(O)R⁵ or —N(H)C(O)N(H)S(O)₂R⁵;

R³ represents $C_{1-6}$ alkyl, $C_{1-6}$ alkoxy, $C_{1-6}$ alkoxy-$C_{1-16}$-alkyl or di-$C_{1-3}$-alkylamino-$C_{1-4}$-alkyl;

R⁴ represents $C_{1-6}$ alkyl, $C_{1-6}$ alkoxy, $C_{1-6}$ alkoxy-$C_{1-6}$-alkyl, $C_{1-3}$ alkoxy-$C_{1-6}$alkoxy, $C_{1-6}$ alkylamino or di-$C_{1-6}$ alkylamino; and R⁵ represents $C_{1-6}$ alkyl, or a pharmaceutically-acceptable salt thereof.

2. A compound as claimed in claim 1, wherein X represents —C(O)— or —S(O)₂—.

3. A compound as claimed in claim 1, wherein R¹ᵃ represents hydrogen, $C_{1-5}$ alkyl, Ar¹, Het¹, or, in the case where X represents —C(O)—, $C_{1-4}$ alkoxy or —C(O)—$C_{1-3}$ alkoxy.

4. A compound as claimed in claim 1, wherein R¹ᵇ represents $C_{1-4}$ alkyl, which alkyl group is optionally substituted by one or more fluoro atoms, optionally substituted Ar¹, $C_{1-2}$ alkyl-Ar² or $C_{1-2}$ alkyl-Het².

5. A compound as claimed in claim 1, wherein Ar¹ is phenyl, optionally substituted by one or more $C_{1-3}$ alkyl groups.

6. A compound as claimed in claim 1, wherein Het¹ is thiophenyl.

7. A compound as claimed in claim 1, wherein Ar² is unsubstituted phenyl.

8. A compound as claimed in claim 1, wherein Het² is pyridinyl.

9. A compound as claimed in claim 1, wherein $Y_1$, $Y_2$, $Y_3$ and $Y_4$ all represent —CH—.

10. A compound as claimed in claim 1, wherein $Z_1$ represents —S— or —CH=CH—.

11. A compound as claimed in claim 10, wherein $Z_1$ represents —S—.

12. A compound as claimed in claim 1, wherein $Z_2$ represents —CH—.

13. A compound as claimed in claim 1, wherein R³ represents $C_{1-4}$ alkyl.

14. A compound as claimed in claim 13, wherein R³ represents iso-butyl.

15. A compound as claimed in claim 1, wherein, when R² represents —S(O)₂N(H)C(O)R⁴, —S(O)₂N(H)S(O)₂R⁴ or —C(O)N(H)S(O)₂R⁴, R⁴ represents n-butoxymethyl, isobutoxy or n-butoxy.

16. A compound as claimed in claim 1, wherein R² represents —S(O)₂N(H)C(O)R⁴.

17. A compound as claimed in claim 16 wherein R⁴ represents n-butoxymethyl, isobutoxy or n-butoxy.

18. A compound as claimed in claim 15 wherein R⁴ represents n-butoxy.

19. A pharmaceutical formulation including a compound as defined in claim 1, or a pharmaceutically acceptable salt thereof, in admixture with a pharmaceutically acceptable adjuvant, diluent or carrier.

* * * * *

UNITED STATES PATENT AND TRADEMARK OFFICE
CERTIFICATE OF CORRECTION

PATENT NO.        : 8,357,710 B2
APPLICATION NO. : 11/918241
DATED             : January 22, 2013
INVENTOR(S)       : Alterman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1474 days.

Signed and Sealed this
First Day of September, 2015

Michelle K. Lee
*Director of the United States Patent and Trademark Office*